(12) United States Patent
Zion et al.

(10) Patent No.: US 8,569,231 B2
(45) Date of Patent: Oct. 29, 2013

(54) SOLUBLE NON-DEPOT INSULIN CONJUGATES AND USES THEREOF

(75) Inventors: Todd C. Zion, Marblehead, MA (US); Thomas M. Lancaster, Stoneham, MA (US)

(73) Assignee: Smartcells, Inc., Rahway, NJ (US)

( * ) Notice: Subject to any disclaimer, the term of this patent is extended or adjusted under 35 U.S.C. 154(b) by 0 days.

(21) Appl. No.: 13/257,507

(22) PCT Filed: Jan. 27, 2010

(86) PCT No.: PCT/US2010/022272
§ 371 (c)(1),
(2), (4) Date: Sep. 19, 2011

(87) PCT Pub. No.: WO2010/107520
PCT Pub. Date: Sep. 23, 2010

(65) Prior Publication Data
US 2012/0010134 A1 Jan. 12, 2012

Related U.S. Application Data

(60) Provisional application No. 61/162,101, filed on Mar. 20, 2009.

(51) Int. Cl.
*A61K 38/28* (2006.01)
*A61P 3/10* (2006.01)

(52) U.S. Cl.
USPC ............................ 514/5.9; 514/6.3; 514/6.9

(58) Field of Classification Search
None
See application file for complete search history.

(56) References Cited

U.S. PATENT DOCUMENTS

| | | |
|---|---|---|
| 3,591,574 A | 7/1971 | Fenichel |
| 3,684,791 A | 8/1972 | Geiger et al. |
| 3,847,890 A | 11/1974 | Green et al. |
| 4,348,387 A | 9/1982 | Brownlee et al. |
| 4,372,948 A | 2/1983 | Yoshikumi et al. |
| 4,377,567 A | 3/1983 | Geho |
| 4,444,683 A | 4/1984 | Kim et al. |
| 4,603,044 A | 7/1986 | Geho et al. |
| 4,863,896 A | 9/1989 | Geho et al. |
| 5,239,062 A | 8/1993 | Blattler et al. |
| 5,395,924 A | 3/1995 | Blattler et al. |
| 5,478,575 A | 12/1995 | Miyazaki et al. |
| 5,527,524 A | 6/1996 | Tomalia et al. |
| 5,563,056 A | 10/1996 | Swan et al. |
| 5,723,589 A | 3/1998 | Miljkovic et al. |
| 5,830,506 A | 11/1998 | Taylor |
| 5,854,208 A | 12/1998 | Jones et al. |
| 5,866,538 A | 2/1999 | Norup et al. |
| 5,902,607 A | 5/1999 | Taylor |
| 5,905,140 A | 5/1999 | Hansen |
| 5,922,675 A | 7/1999 | Baker et al. |
| 5,948,751 A | 9/1999 | Kimer et al. |
| 5,994,517 A | 11/1999 | Ts'o et al. |
| 6,034,054 A | 3/2000 | DeFelippis et al. |
| 6,180,757 B1 | 1/2001 | Bogsnes |
| 6,214,547 B1 | 4/2001 | Kjeldsen et al. |
| 6,323,311 B1 | 11/2001 | Liu et al. |
| 6,342,225 B1 | 1/2002 | Jones et al. |
| 6,410,053 B1 | 6/2002 | Taylor |
| 6,500,645 B1 | 12/2002 | Kjeldsen et al. |
| 6,521,738 B2 | 2/2003 | Kjeldsen et al. |
| 6,551,992 B1 | 4/2003 | DeFelippis et al. |
| 6,777,207 B2 | 8/2004 | Kjeldsen et al. |
| 6,844,166 B1 | 1/2005 | Wolf |
| 6,869,930 B1 | 3/2005 | Havelund et al. |
| RE39,055 E | 4/2006 | Jones et al. |
| 7,063,863 B2 | 6/2006 | Taylor |
| 7,087,408 B2 | 8/2006 | Kjeldsen et al. |
| 7,105,314 B2 | 9/2006 | Kjeldsen |
| 7,316,999 B2 | 1/2008 | Hoeg-Jensen et al. |
| 7,317,000 B2 | 1/2008 | Hoeg-Jensen et al. |
| 7,423,014 B2 | 9/2008 | Ekwuribe et al. |
| 7,531,191 B2 | 5/2009 | Zion et al. |
| 7,687,608 B2 | 3/2010 | Lancaster et al. |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Baudys, et al., "Physical Stabilization of Insulin by Glycosylation" *J Pharma Sci* (1995) 64: 28-33.

(Continued)

*Primary Examiner* — Gyan Chandra

(74) *Attorney, Agent, or Firm* — John David Reilly; Immac J. Thampoe

(57) ABSTRACT

In one aspect, the disclosure provides a conjugate comprising an insulin molecule having an A-chain and a B-chain; an affinity ligand covalently bound to the A-chain; and a monovalent glucose binding agent covalently bound to the B-chain, wherein the affinity ligand competes with glucose for non-covalent binding with the monovalent glucose binding agent. In the absence of glucose, the monovalent glucose binding agent binds the affinity ligand to produce a "closed" inactive form of the insulin molecule. When free glucose is added, it competes with the affinity ligand for binding with the monovalent glucose binding agent to produce an "open" active form of the insulin molecule. The monovalent glucose binding agent and affinity ligand are covalently bound to the insulin molecule. The disclosure also provides methods of using these conjugates and methods of making these conjugates. In another aspect, the disclosure provides exemplary conjugates. The disclosure also provides alternative conjugates that are not necessarily activated by glucose.

12 Claims, 6 Drawing Sheets

(56) References Cited

U.S. PATENT DOCUMENTS

| | | |
|---|---|---|
| 2006/0019874 A1 | 1/2006 | Radhakrishnan et al. |
| 2006/0216265 A1 | 9/2006 | Goodman et al. |
| 2006/0247154 A1 | 11/2006 | Palmieri et al. |
| 2007/0099820 A1* | 5/2007 | Lancaster et al. .......... 514/3 |
| 2007/0207498 A1 | 9/2007 | Palmieri et al. |
| 2009/0053167 A1 | 2/2009 | DeFrees |
| 2009/0137454 A1 | 5/2009 | Fynbo et al. |

FOREIGN PATENT DOCUMENTS

| | | |
|---|---|---|
| EP | 0119650 | 9/1984 |
| EP | 0725648 | 8/1996 |
| RU | 2381238 | 8/2009 |
| WO | WO81/00354 | 2/1981 |
| WO | WO84/01896 | 5/1984 |
| WO | WO90/10645 | 9/1990 |
| WO | WO99/52934 | 10/1999 |
| WO | WO01/92334 | 12/2001 |
| WO | WO03/035011 | 5/2003 |
| WO | WO03/047462 | 6/2003 |
| WO | WO03/048915 | 6/2003 |
| WO | WO03/074087 | 9/2003 |
| WO | WO2004/057002 | 7/2004 |
| WO | WO2006/008238 | 1/2006 |
| WO | WO2006/082184 | 8/2006 |
| WO | WO2006/088473 | 8/2006 |
| WO | WO2006/102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2009/033588 | 3/2009 |
| WO | WO2009/059450 | 5/2009 |
| WO | WO2009/089396 | 7/2009 |
| WO | WO2009/104199 | 8/2009 |
| WO | WO2011/000823 | 1/2011 |

OTHER PUBLICATIONS

Brownlee & Cerami, "A Glucose-Controlled-Insulin-Delivery-System: Semisynthetic Insulin Bound to Lectin" *Diabetes* (1983) 32: 499-504.

Brownlee & Cerami, "Glycosylated Insulin Complexed to Concanavalin A" *Science* (1979) 206: 1190-1191.

Dea, et al., "Albumin Binding of Acylated Insulin (NN304) Does Not Deter Action to Stimulate Glucose Uptake" *Diabetes* (2002) 51: 762-769.

Eggert, et al., "A New Glucose Selective Fluorescent Bisboronic Acid" *J Org Chem* (1999) 64: 3846-3852.

Heinnemann, et al., "Time-action profile of the soluble, fatty acid acylated, long acting insulin analogue NN304" *Diabetic Med* (1999) 16: 332-338.

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoy Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

* cited by examiner

| Sequence | SEQ ID NO. |
|---|---|
| GGGAGUCGACCGACCAGAAUUAUGUGCGUCUACAUCUAGACUCAU | 1 |
| GGGAGUCGACCGACCAGAAUUAUCUGCGUGU-UAUCUUCAAUCAUUAACAGUACACUUAAUAUGUGCGUCACUCUAGACUCAU | 2 |
| GGGAGUCGACCGACCAGAAUUAUCUGCGUGU-UAUCCCCAAUCAUUAACAGUACACUUAAUAUGUGCGUCUACAUCUAGACUCAU | 3 |
| GGGAGUCGACCGACCAGAAUUAUCUGCGUGU-UAUCCCCAGUCAUUAACAGUACACUUAAUAUGUGCGUCUACAUCUAGACUCAU | 7 |
| GGGAGUCGACCGACCAGAAUUAUCCGCGUGU-UAUCCCCAAUCAUUAACAGUACACUUAAUAUGUGCGUCUACAUCUAGACUCAU | 5 |
| GGGAGUCGACCGACCAGAAUAUACAGUACGGGG-GUGAUCACCAAUGCUGAAUGCAGAAGCGUAUGUGCGUCUACAUCUAGACUCAU | 4 |
| GGGAGUCGACCGACCAGAGAAGUCAGGAUAGGU-GCAAGAAUGCGAAAUUCGCAGGCUGGUGUAUGUGCGUCUACAUCUAGACUCAU | 6 |

Figure 5

SEQUENCE LISTING

```
<160> NUMBER OF SEQ ID NOS: 12

<210> SEQ ID NO 1
<211> LENGTH: 45
<212> TYPE: DNA
<213> ORGANISM: Artificial Sequence
<220> FEATURE:
<223> OTHER INFORMATION: Monoclonal aptamer

<400> SEQUENCE: 1
gggagucgac cgaccagaau uaugugcguc uacaucuaga cucau          45

<210> SEQ ID NO 2
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 2
gggagucgac cgaccagaau uaucugcgug uuaucuucaa ucauuaacag uacacuuaau          60
augugcgucu acaucuagac ucau                                                 84

<210> SEQ ID NO 3
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 3
```

```
gggagucgac cgaccagaau uaucugcgug uuauccccaa ucauuaacag uacacuuaau    60
augugcgucu acaucuagac ucau                                          84

<210> SEQ ID NO 4
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 4
gggagucgac cgaccagaau acaguacggg ggugaucacc aaugcugaau gcagaagcgu    60
augugcgucu acaucuagac ucau                                          84

<210> SEQ ID NO 5
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 5
gggagucgac cgaccagaau auccgcgug uuauccccaa ucauuaacag uacacuuaau     60
augugcgucu acaucuagac ucau                                          84

<210> SEQ ID NO 6
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 6
gggagucgac cgaccagaag ucaggauagg ugcaagaaug cgaaauucgc aggcuggugu    60
augugcgucu acaucuagac ucau                                          84

<210> SEQ ID NO 7
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 7
gggagucgac cgaccagaau uaucugcgug uuauccccag ucauuaacag uacacuuaau    60
augugcgucu acaucuagac ucau                                          84

<210> SEQ ID NO 8
<211> LENGTH: 40
<212> TYPE: DNA
<213> ORGANISM: Artificial Sequence
<220> FEATURE:
<223> OTHER INFORMATION: Consensus aptamer sequence
<220> FEATURE:
<221> NAME/KEY: misc_feature
<222> LOCATION: (1)..(1)
<223> OTHER INFORMATION: t/u
<220> FEATURE:
<221> NAME/KEY: misc_feature
<222> LOCATION: (2)..(2)
<223> OTHER INFORMATION: t/u
<220> FEATURE:
<221> NAME/KEY: misc_feature
<222> LOCATION: (4)..(4)
<223> OTHER INFORMATION: t/u
<220> FEATURE:
```

<221> NAME/KEY: misc_feature
<222> LOCATION: (10)..(10)
<223> OTHER INFORMATION: t/u
<220> FEATURE:
<221> NAME/KEY: misc_feature
<222> LOCATION: (12)..(12)
<223> OTHER INFORMATION: t/u
<220> FEATURE:
<221> NAME/KEY: misc_feature
<222> LOCATION: (13)..(13)
<223> OTHER INFORMATION: t/u
<220> FEATURE:
<221> NAME/KEY: misc_feature
<222> LOCATION: (15)..(15)
<223> OTHER INFORMATION: t/u
<220> FEATURE:
<221> NAME/KEY: misc_feature
<222> LOCATION: (22)..(22)
<223> OTHER INFORMATION: t/u
<220> FEATURE:
<221> NAME/KEY: misc_feature
<222> LOCATION: (25)..(25)
<223> OTHER INFORMATION: t/u
<220> FEATURE:
<221> NAME/KEY: misc_feature
<222> LOCATION: (26)..(26)
<223> OTHER INFORMATION: t/u
<220> FEATURE:
<221> NAME/KEY: misc_feature
<222> LOCATION: (32)..(32)
<223> OTHER INFORMATION: t/u
<220> FEATURE:
<221> NAME/KEY: misc_feature
<222> LOCATION: (37)..(37)
<223> OTHER INFORMATION: t/u
<220> FEATURE:
<221> NAME/KEY: misc_feature
<222> LOCATION: (38)..(38)
<223> OTHER INFORMATION: t/u

<400> SEQUENCE: 8
nnancygcgn gnnancyyca rncannaaca gnacacnnaa        40

<210> SEQ ID NO 9
<211> LENGTH: 40
<212> TYPE: DNA
<213> ORGANISM: Artificial Sequence
<220> FEATURE:
<223> OTHER INFORMATION: Consensus aptamer sequence
<220> FEATURE:
<221> NAME/KEY: misc_feature
<222> LOCATION: (1)..(1)
<223> OTHER INFORMATION: t/u
<220> FEATURE:
<221> NAME/KEY: misc_feature
<222> LOCATION: (6)..(6)
<223> OTHER INFORMATION: t/u
<220> FEATURE:
<221> NAME/KEY: misc_feature
<222> LOCATION: (14)..(14)
<223> OTHER INFORMATION: t/u
<220> FEATURE:
<221> NAME/KEY: misc_feature
<222> LOCATION: (17)..(17)
<223> OTHER INFORMATION: t/u
<220> FEATURE:
<221> NAME/KEY: misc_feature
<222> LOCATION: (24)..(24)
<223> OTHER INFORMATION: t/u
<220> FEATURE:
<221> NAME/KEY: misc_feature
<222> LOCATION: (27)..(27)
<223> OTHER INFORMATION: t/u
<220> FEATURE:
<221> NAME/KEY: misc_feature
<222> LOCATION: (31)..(31)
<223> OTHER INFORMATION: t/u

```
<400> SEQUENCE: 9
nacagnacgg gggngancac caangcngaa ngcagaagcg                              40

<210> SEQ ID NO 10
<211> LENGTH: 40
<212> TYPE: DNA
<213> ORGANISM: Artificial Sequence
<220> FEATURE:
<223> OTHER INFORMATION: Consensus aptamer sequence
<220> FEATURE:
<221> NAME/KEY: misc_feature
<222> LOCATION: (2)..(2)
<223> OTHER INFORMATION: t/u
<220> FEATURE:
<221> NAME/KEY: misc_feature
<222> LOCATION: (8)..(8)
<223> OTHER INFORMATION: t/u
<220> FEATURE:
<221> NAME/KEY: misc_feature
<222> LOCATION: (12)..(12)
<223> OTHER INFORMATION: t/u
<220> FEATURE:
<221> NAME/KEY: misc_feature
<222> LOCATION: (20)..(20)
<223> OTHER INFORMATION: t/u
<220> FEATURE:
<221> NAME/KEY: misc_feature
<222> LOCATION: (27)..(27)
<223> OTHER INFORMATION: t/u
<220> FEATURE:
<221> NAME/KEY: misc_feature
<222> LOCATION: (28)..(28)
<223> OTHER INFORMATION: t/u
<220> FEATURE:
<221> NAME/KEY: misc_feature
<222> LOCATION: (36)..(36)
<223> OTHER INFORMATION: t/u
<220> FEATURE:
<221> NAME/KEY: misc_feature
<222> LOCATION: (39)..(39)
<223> OTHER INFORMATION: t/u

<400> SEQUENCE: 10
gncagganag gngcaagaan gcgaaanncg caggcnggng                              40

<210> SEQ ID NO 11
<211> LENGTH: 21
<212> TYPE: PRT
<213> ORGANISM: Homo sapiens

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 30
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

SOLUBLE NON-DEPOT INSULIN CONJUGATES AND USES THEREOF

RELATED APPLICATIONS

This application claims priority to International Application No. PCT/US2010/022272, filed Jan. 27, 2010 and which claims benefit of U.S. Provisional Application No. 61/162,101 filed Mar. 20, 2009, the content of each of which is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23033USPCT-SEQTXT-07SEPT2011.txt", creation date of Sep. 7, 2011 and a size of 5 KB. This sequence listing submitted via EFS-Web is part of the specification and is herein incorporated by reference in its entirety.

BACKGROUND

The majority of "controlled-release" drug delivery systems operate by slowing or delaying the release of a drug post-administration. While these systems are useful for certain types of drugs (e.g., because they lead to fewer peaks and troughs in the serum profile, reduced side-effects, etc.) they are unsuitable for drugs that require more complex release profiles. For example, the treatment of diabetes mellitus with injectable insulin is a well-known and studied case where gradual slow release of insulin is ineffective. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient (i.e., a truly "controlled-release" system). As a result, there remains a need in the art for alternative controlled-release insulin delivery systems. The present disclosure provides such systems.

SUMMARY

In one aspect, the disclosure provides a conjugate comprising an insulin molecule having an A-chain and a B-chain; an affinity ligand covalently bound to the A-chain; and a monovalent glucose binding agent covalently bound to the B-chain, wherein the affinity ligand competes with glucose for non-covalent binding with the monovalent glucose binding agent. In the absence of glucose, the monovalent glucose binding agent binds the affinity ligand to produce a "closed" inactive form of the insulin molecule. When free glucose is added, it competes with the affinity ligand for binding with the monovalent glucose binding agent to produce an "open" active form of the insulin molecule. The monovalent glucose binding agent and affinity ligand are covalently bound to the insulin molecule. The disclosure also provides methods of using these conjugates and methods of making these conjugates. In another aspect, the disclosure provides exemplary conjugates.

As discussed in more detail below, it is to be understood that the conjugates that are disclosed herein may be used to deliver an insulin molecule in response to saccharides other than glucose (and/or to non-saccharide target molecules). In particular, in certain embodiments, conjugates may be used that are activated by administration of an exogenous saccharide (i.e., instead of or in addition to being controlled by fluctuations in endogenous glucose).

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, $3^{rd}$ Edition, Cambridge University Press, Cambridge, 1987.

Acyl—As used herein, the term "acyl," refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxy-alkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., $-(CH_2)_z-$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring.

Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branched)alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}P$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Aptamer—As used herein, the term "aptamer" refers to a polynucleotide or polypeptide that binds specifically to a target molecule. In general, an aptamer is said to "bind specifically" to its target molecule (e.g., glucose) if it associates at a detectable level with the target molecule and does not associate detectably with unrelated molecular entities (e.g., molecules which share no common structural features with the target molecule) under similar conditions. Specific association between a target molecule and an aptamer will typically be dependent upon the presence of a particular structural feature of the target molecule such as an epitope recognized by the aptamer. Generally, if an aptamer is specific for epitope A, the presence of a molecule containing epitope A or the presence of free unlabeled epitope A in a reaction containing both free labeled epitope A and the aptamer thereto, will reduce the amount of labeled epitope A that binds to the aptamer. In general, it is to be understood that specificity need not be absolute. Indeed, it is well known in the art that aptamers may cross-react with other epitopes in addition to the target epitope. Such cross-reactivity may be acceptable depending upon the application for which the aptamer is to be used. Thus the degree of specificity of an aptamer will depend on the context in which it is being used. It is also to be understood that specificity may be evaluated in the context of additional factors such as the affinity of the aptamer for the target molecule versus the affinity of the aptamer for non-target molecules.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Exogenous—As used herein, an "exogenous" molecule is one which is not present at significant levels in a patient unless administered to the patient. In certain embodiments the patient is a mammal, e.g., a human, a dog, a cat, a rat, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Lectin—As used herein, a "lectin" is a protein that binds with specificity to saccharides and polysaccharides. A lectin can be of any origin (e.g., plant, animal or other). In certain embodiments a lectin can be isolated from a natural source. In other embodiments a lectin can be produced synthetically or recombinantly.

Percentage homology—As used herein, the terms "percentage homology" refer to the percentage of sequence identity between two sequences after optimal alignment as defined in the present disclosure. For example, two nucleotide sequences are said to be "identical" if the sequence of nucleotides in the two sequences is the same when aligned for maximum correspondence as described below. Sequence comparisons between two nucleotide sequences are typically performed by comparing sequences of two optimally aligned sequences over a region or "comparison window" to identify and compare regions of sequence similarity. Optimal alignment of sequences for comparison may be conducted by the local homology algorithm of Smith and Waterman, *Ad. App. Math.* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci. USA* 85:2444 (1988), by computerized implementation of these algorithms, or by visual inspection.

Percentage of sequence identity—"Percentage of sequence identity" is determined by comparing two optimally aligned sequences over a comparison window, where the portion of the nucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide residue occurs in both sequences to yield the number of matched positions, dividing the number of matched positions by the total number of positions in the window of comparison and multiplying the result by 100 to yield the percentage of sequence identity. This definition of sequence identity given above is the definition that would be used by one of ordinary skill in the art. The definition by itself does not need the help of any algorithm. The algorithms are only helpful to facilitate the optimal alignments of sequences, rather than calculate sequence identity. From this definition, it follows that there is a well defined and only one value for the sequence identity between two compared sequences which value corresponds to the value obtained for the optimal alignment.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWINGS

FIG. 1A shows the dynamic non-covalent interaction which exists between the affinity ligand on the A-chain and the monovalent glucose binding agent on the B-chain. FIG. 1B shows the "closed" inactive insulin conjugate when insufficient glucose is present to disrupt the interaction between the affinity ligand and the monovalent glucose binding agent. FIG. 1C shows the "open" active insulin conjugate when sufficient glucose is present to disrupt the interaction between the affinity ligand and the monovalent glucose binding agent.

FIG. 3A shows a conjugate which includes a PEG moiety on the monovalent glucose binding agent. FIG. 3B shows a conjugate which includes a fatty acyl chain or a PEG moiety linked to Phe-B29.

FIG. 5: shows the sequence homology of several exemplary 84 bp monoclonal aptamers as compared to monoclonal 2.

DETAILED DESCRIPTION OF CERTAIN EMBODIMENTS

This application refers to a number of documents including patent and non-patent documents. The entirety of each of these documents is incorporated herein by reference.

Figure 1:
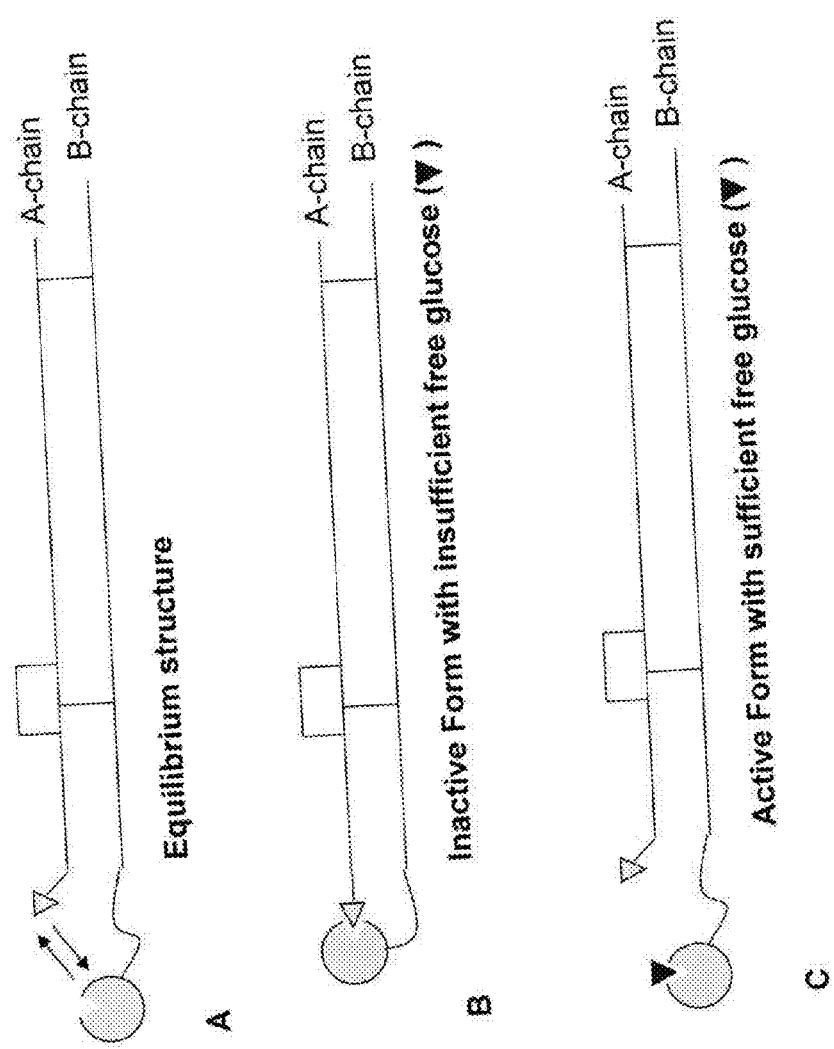
FIG. 1: illustrates one embodiment of an inventive conjugate.

In one aspect, the disclosure provides a conjugate which includes an affinity ligand bound to the A-chain of an insulin molecule and a monovalent glucose binding agent bound to the B-chain, wherein the affinity ligand competes with glucose for non-covalent binding with the monovalent glucose binding agent (see FIG. 1A). In the absence of glucose, the monovalent glucose binding agent binds the affinity ligand to produce a "closed" inactive form of the insulin molecule (see FIG. 1B). When free glucose is added, it competes with the affinity ligand for binding with the monovalent glucose binding agent to produce an "open" active form of the insulin molecule (see FIG. 1C). The glucose concentration at which the switch from inactive to active occurs can be tailored based on the relative affinities of glucose and the A-chain ligand for the B-chain glucose binding agent. As a result, the conjugate is activated in a manner which is directly tied to the local concentration of glucose. In general, the monovalent glucose binding agent and affinity ligand are covalently bound to the insulin. The disclosure also provides methods of using these conjugates and methods of making these conjugates. In another aspect, the disclosure provides exemplary conjugates.

These inventive conjugates are supported by three observations:

(a) B-chain substitution is permissible with large size molecules without significant impact on insulin bioactivity (e.g., see Mei et al., *Pharm. Res.* 16: 1680-1686, 1999 and references cited therein, Tsai et al., *J. Pharm. Sci.* 86: 1264-1268, 1997, Hinds and Kim, *Advanced Drug Delivery Reviews*. 54: 505-530, 2002, and Hashimoto et al., *Pharm. Res.* 6: 171-176, 1989);

(b) A-chain substitution is less permissible but small size substitutions can be made without having a significant impact on insulin bioactivity (e.g., Baudys and coworkers report an activity of ~1 U/mg for insulin substituted at the Gly-A1 with a ~40,000 g/mol carboxymethyl-dextran as opposed to ~22 U/mg for insulin substitute with a 180 g/mol glucose unit and ~25 U/mg for unsubstituted insulin, see Baudys et al., *Bioconjugate Chem.* 9: 176-183, 1998; in addition, Gliemann and Gammeltoft, *Diabetologia* 10:105-113, 1974 describe bioactive insulins that are conjugated to low molecular weight entities at the Gly-A1); and (c) connections between the A- and B-chain usually eliminate insulin bioactivity (e.g., see Gliemann and Gammeltoft, *Diabetologia* 10:105-113, 1974).

The present disclosure is based in part on the realization that by creating a glucose sensitive reversible connection between the A- and B-chain we could create a glucose sensitive switch between active and inactive forms of an insulin molecule. We also realized that in order to preserve bioactivity in the "open" form, we needed to place the smaller affinity ligand component on the A-chain with the larger monovalent glucose binding agent on the B-chain. Below we described various embodiments of the insulin molecule, affinity ligand and monovalent glucose binding agent components.

As discussed in more detail below, it is to be understood that the conjugates that are disclosed herein may be used to deliver an insulin molecule in response to saccharides other than glucose (and/or to non-saccharide target molecules). In particular, in certain embodiments, conjugates may be used that are activated by administration of an exogenous saccharide (i.e., instead of or in addition to being controlled by fluctuations in endogenous glucose).

Insulin Molecule

Figure 6:
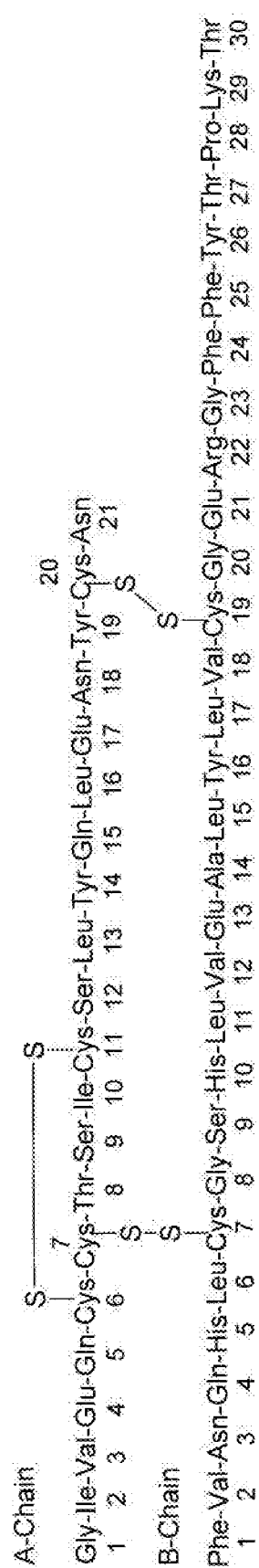
FIG. 6: shows the structure of wild-type human insulin.

As used herein, an "insulin molecule" encompasses both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids). In general, a bioactive mutant form of insulin will typically differ from wild-type insulin by 1-10 (e.g., from 1-5 or 1-2) amino acid substitutions, additions or deletions. The wild-type sequence of human insulin (A-chain and B-chain) is shown below and in FIG. 6.

```
A-Chain (SEQ ID NO: 11):
GIVEQCCTSICSLYQLENYCN

B-Chain (SEQ ID NO: 12):
FVNQHLCGSHLVEALYLVCGERGFFYTPKT
```

Human insulin differs from rabbit, porcine, bovine, and sheep insulin only in amino acids A8, A9, A10, and B30 (see table below).

| | Amino Acid Position | | | |
|---|---|---|---|---|
| Insulin | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue (Lys$^{B3}$Glu$^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include Arg$^{A0}$-human insulin, Ar$^{B31}$Arg$^{B32}$-human insulin, Gly$^{A21}$Arg$^{B31}$Arg$^{B32}$ human insulin, Arg$^{A0}$Arg$^{B31}$Arg$^{B32}$-human insulin, and Arg$^{A0}$Gly$^{A21}$Arg$^{B31}$Arg$^{B32}$ human insulin. By way of further example, insulin glargine (LANTUS®) is an exemplary long acting insulin mutant in which Asp$^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., Gly$^{A21}$-human insulin, Gly$^{A21}$Arg$^{B31}$-human insulin, Arg$^{B31}$Arg$^{B32}$-human insulin, Arg$^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des (B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, Asn$^{A18}$, Asn$^{A21}$, or Asn$^{B3}$, or any combination of those residues, may be replaced by aspartic acid or glutamic acid. Gln$^{A15}$ or Gln$^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid (His$^{B10}$→Asp$^{B10}$); replacement of the phenylalanine residue at position B1 with aspartic acid (Phe$^{B1}$→Asp$^{B1}$); replacement of the threonine residue at position B30 with alanine (Thr$^{B30}$→Ala$^{B30}$); replacement of the tyrosine residue at position B26 with alanine (Tyr$^{B26}$→Ala$^{B26}$); and replacement of the serine residue at position B9 with aspartic acid (Ser$^{B9}$→Asp$^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which Thr$^{B30}$ has been deleted, and a C14 fatty acid chain (myristic acid) has been attached to Lys$^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

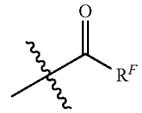

where R$^F$ is hydrogen or a C$_{1-30}$ alkyl group. In some embodiments, R$^F$ is a C$_{1-20}$ alkyl group, a C$_{3-19}$ alkyl group, a C$_{5-18}$ alkyl group, a C$_{6-17}$ alkyl group, a C$_{8-16}$ alkyl group, a C$_{10-15}$ alkyl group, or a C$_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of Lys$^{B28}$ is conjugated to the fatty acid moiety. In certain embodiments, position B3 of the insulin molecule is Lys and the epsilon-amino group of Lys$^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which Thr$^{B30}$ has been deleted, and a C14 fatty acid chain (myristic acid) is attached to Lys$^{B29}$.

In certain embodiments, an insulin molecule of the present disclosure comprises the mutations and/or chemical modifications of one of the following insulin molecules: Lys$^{B28}$Pro$^{B29}$-human insulin (insulin lispro), Asp$^{B28}$-human-insulin (insulin aspart), Lys$^{B3}$Glu$^{B29}$-human insulin (insulin glulisine), Arg$^{B31}$Arg$^{B32}$-human insulin (insulin glargine), N$^{\epsilon B29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: N$^{\epsilon B29}$-palmitoyl-human insulin, N$^{\epsilon B29}$-myrisotyl-human insulin, N$^{\epsilon B28}$-palmitoyl-Lys$^{B28}$Pro$^{B29}$-human insulin, N$^{\epsilon B28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-palmitoyl-des(B30)-human insulin, N$^{\epsilon B30}$-myristoyl-Thr$^{B29}$Lys$^{B30}$-human insulin, N$^{\epsilon B30}$-palmitoyl-Thr$^{B29}$Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(w-carboxyheptadecanoyl)-human insulin.

In certain embodiments, an insulin molecule of the present disclosure comprises the mutations and/or chemical modifications of one of the following insulin molecules: N$^{\epsilon B29}$-octanoyl-human insulin, N$^{\epsilon B29}$-myristoyl-Gly$^{A21}$Arg$^{B31}$Arg$^{B31}$-human insulin, N$^{\epsilon B29}$-myristoyl-Gly$^{A21}$Gln$^{B3}$Arg$^{B31}$Arg$^{B32}$-human insulin, N$^{\epsilon B29}$-myristoyl-Arg$^{A0}$Gly$^{A21}$Arg$^{B31}$Arg$^{B32}$-human insulin, N$^{\epsilon B29}$-Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$^{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B31}$Arg$^{B32}$-human insulin, N$^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B29}$-tridecanoyl-des(B30)-human insulin, N$^{\epsilon B29}$-tetradecanoyl-des(B30)-human insulin, N$^{\epsilon B29}$-decanoyl-des(B30)-human insulin, N$^{\epsilon B29}$-dodecanoyl-des(B30)-human insulin, N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$-Gln$^{B3}$-des(B30)-human insulin, N$^{\epsilon B29}$-dodecanoyl-Gly$^{A21}$-Gln$^{B3}$-des(B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des(B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl-Ala$^{A21}$Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Glu$^{B30}$-human insulin, N$^{\epsilon B29}$-tetradecanoyl-Glu$^{B30}$-human insulin, N$^{\epsilon B29}$-decanoyl-Glu$^{B30}$-human insulin, N$^{\epsilon B29}$-dodecanoyl-Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin. In certain embodiments, an insulin molecule of the present disclosure comprises the mutations and/or chemical modifications of one of the following insulin molecules: $N^{\epsilon B29}$-tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Gln$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{B30}$-human insulin, $N^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In certain embodiments, an insulin molecule of the present disclosure comprises the mutations and/or chemical modifications of one of the following insulin molecules: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin molecule of the present disclosure comprises the mutations and/or chemical modifications of one of the following insulin molecules: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In certain embodiments, an insulin molecule of the present disclosure comprises the mutations and/or chemical modifications of one of the following insulin molecules: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin molecule of the present disclosure comprises the mutations and/or chemical modifications of one of the following insulin molecules: $N^{\epsilon B29}$-pentanoyl-human insulin, $N^{\alpha B1}$-pentanoyl-human insulin, $N^{\alpha A1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N^{\alpha B1}$-pentanoyl-human insulin.

In certain embodiments, an insulin molecule of the present disclosure comprises the mutations and/or chemical modifications of one of the following insulin molecules: $N^{\epsilon B29}$-hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin molecule of the present disclosure comprises the mutations and/or chemical modifications of one of the following insulin molecules: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In certain embodiments, an insulin molecule of the present disclosure comprises the mutations and/or chemical modifications of one of the following insulin molecules: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin molecule of the present disclosure comprises the mutations and/or chemical modifications of one of the following insulin molecules: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin molecule of the present disclosure comprises the mutations and/or chemical modifications of one of the following insulin molecules: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin molecule of the present disclosure comprises the mutations and/or chemical modifications of one of the following insulin molecules: $N^{\epsilon B28}$-formyl-Lys$^{B28}$Pro$^{B29}$-human insulin, $N^{\epsilon B21}$-formyl-Lys$^{B28}$Pro$^{B29}$-human insulin, $N^{\alpha A1}$-formyl-Lys$^{B28}$Pro$^{B29}$-human insulin, $N^{\epsilon B28}$-formyl-$N^{\alpha B1}$-formyl-Lys$^{B28}$Pro$^{B29}$-human insulin, $N^{\epsilon B28}$-formyl-$N^{\alpha A1}$-formyl-Lys$^{B28}$Pro$^{B29}$-human insulin, $N^{\alpha A1}$-formyl-$N^{\alpha B1}$-formyl-Lys$^{B28}$Pro$^{B29}$-human insulin, $N^{\epsilon B28}$-formyl-$N^{\alpha A1}$-formyl-$N^{\alpha B1}$-formyl-Lys$^{B28}$Pro$^{B29}$-human insulin, $N^{\epsilon B29}$-acetyl-Lys$^{B28}$Pro$^{B29}$-human insulin, $N^{\alpha B1}$-acetyl-Lys$^{B28}$Pro$^{B29}$-human insulin, $N^{\alpha A1}$-acetyl-Lys$^{B28}$Pro$^{B29}$-human insulin, $N^{\epsilon B28}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon 828}$-acetyl-$N^{\alpha A1}$-acetyl-Lys$^{B28}$Pro$^{B29}$-human insulin, $N^{\alpha A1}$- acetyl-$N^{\alpha B1}$-acetyl-Lys$^{B28}$Pro$^{B29}$-human insulin, $N^{\epsilon B28}$-acetyl-$N^{\alpha A1}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-propionyl-Lys$^{B28}$Pro$^{B29}$-human insulin, $N^{\alpha B1}$-propionyl-Lys$^{B28}$Pro$^{B29}$-human insulin, $N^{\alpha A1}$-propionyl-Lys$^{B28}$Pro$^{B29}$-human insulin, $N^{\epsilon B28}$-propionyl-$N^{\alpha B1}$-propionyl-Lys$^{B28}$Pro$^{B29}$-human insulin, $N^{\epsilon B28}$-propionyl-$N^{\alpha A1}$-propionyl-Lys$^{B28}$Pro$^{B29}$-human insulin, $N^{\alpha A1}$-propionyl-$N^{\alpha B1}$-propionyl-Lys$^{B28}$Pro$^{B29}$-human insulin, $N^{\epsilon B28}$-propionyl-$N^{\alpha A1}$-propionyl-$N^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-butyryl-Lys$^{B28}$Pro$^{B29}$-human insulin, $N^{\alpha B1}$-butyryl-Lys$^{B28}$Pro$^{B29}$-human insulin, $N^{\alpha A1}$-butyryl-Lys$^{B28}$Pro$^{B29}$-human insulin, $N^{\epsilon B28}$-butyryl-$N^{\alpha B1}$-butyryl-Lys$^{B28}$Pro$^{B29}$-human insulin, $N^{\epsilon B28}$-butyryl-$N^{\alpha A1}$-butyryl-Lys$^{B28}$Pro$^{B29}$-human insulin, $N^{\alpha A1}$-butyryl-$N^{\alpha B1}$-butyryl-Lys$^{B28}$Pro$^{B29}$-human insulin, $N^{\epsilon B28}$-butyryl-$N^{\alpha A1}$-butyryl-$N^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-pentanoyl-Lys$^{B28}$Pro$^{B29}$-human insulin, $N^{\alpha B1}$-pentanoyl-Lys$^{B28}$Pro$^{B29}$-human insulin, $N^{\alpha A1}$-pentanoyl-Lys$^{B28}$Pro$^{B29}$-human insulin, $N^{\epsilon B28}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-Lys$^{B28}$Pro$^{B29}$-human insulin, $N^{\alpha A1}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-$N^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-hexanoyl-Lys$^{B28}$Pro$^{B29}$-human insulin, $N^{\alpha B1}$-hexanoyl-Lys$^{B28}$Pro$^{B29}$-human insulin, $N^{\alpha A1}$-hexanoyl-Lys$^{B28}$Pro$^{B29}$-human insulin, $N^{\epsilon B28}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-Lys$^{B28}$Pro$^{B29}$-human insulin, $N^{\alpha A1}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-$N^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-heptanoyl-Lys$^{B28}$Pro$^{B29}$-human insulin, $N^{\alpha B1}$-heptanoyl-Lys$^{B28}$Pro$^{B29}$-human insulin, $N^{\alpha A1}$-heptanoyl-Lys$^{B28}$Pro$^{B29}$-human insulin, $N^{\epsilon B28}$-heptanoyl-$N^{\alpha B1}$-heptanoyl-Lys$^{B28}$Pro$^{B29}$-human insulin, $N^{\epsilon B28}$-heptanoyl-$N^{\alpha A1}$-heptanoyl-Lys$^{B28}$Pro$^{B29}$-human insulin, $N^{\alpha A1}$-heptanoyl-$N^{\alpha B1}$-heptanoyl-Lys$^{B28}$Pro$^{B29}$-human insulin, $N^{\epsilon B28}$-heptanoyl-$N^{\alpha A1}$-heptanoyl-$N^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-octanoyl-Lys$^{B28}$Pro$^{B29}$-human insulin, $N^{\alpha B1}$-octanoyl-Lys$^{B28}$Pro$^{B29}$-human insulin, $N^{\alpha A1}$-octanoyl-Lys$^{B28}$Pro$^{B29}$-human insulin, $N^{\epsilon B28}$-octanoyl-$N^{\alpha B1}$-octanoyl-Lys$^{B28}$Pro$^{B29}$-human insulin, $N^{\epsilon B28}$-octanoyl-$N^{\alpha A1}$-octanoyl-Lys$^{B28}$Pro$^{B29}$-human insulin, $N^{\alpha A1}$-octanoyl-$N^{\alpha B1}$-octanoyl-Lys$^{B28}$Pro$^{B29}$-human insulin, $N^{\epsilon B28}$-octanoyl-$N^{\alpha A1}$-octanoyl-$N^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-nonanoyl-Lys$^{B28}$Pro$^{B29}$-human insulin, $N^{\alpha B1}$-nonanoyl-Lys$^{B28}$Pro$^{B29}$-human insulin, $N^{\alpha A1}$-nonanoyl-Lys$^{B28}$Pro$^{B29}$-human insulin, $N^{\epsilon B28}$-nonanoyl-$N^{\alpha B1}$-nonanoyl-Lys$^{B28}$Pro$^{B29}$-human insulin, $N^{\epsilon B28}$-nonanoyl-$N^{\alpha A1}$-nonanoyl-Lys$^{B28}$Pro$^{B29}$-human insulin, $N^{\alpha A1}$-nonanoyl-$N^{\alpha B1}$-nonanoyl-Lys$^{B28}$Pro$^{B29}$-human insulin, $N^{\epsilon B28}$-nonanoyl-$N^{\alpha A1}$-nonanoyl-$N^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-decanoyl-Lys$^{B28}$Pro$^{B29}$-human insulin, $N^{\alpha B1}$-decanoyl-Lys$^{B28}$Pro$^{B29}$-human insulin, $N^{\alpha A1}$-decanoyl-Lys$^{B28}$Pro$^{B29}$-human insulin, $N^{\epsilon B28}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-Lys$^{B28}$Pro$^{B29}$-human insulin, $N^{\alpha A1}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-$N^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B29}$-pentanoyl-Gly$^{A21}$Arg$^{B31}$Arg$^{B32}$-human insulin, $N^{\alpha B1}$-hexanoyl-Gly$^{A21}$Arg$^{B31}$Arg$^{B32}$-human insulin, $N^{\alpha A1}$-heptanoyl-Gly$^{A21}$Arg$^{B31}$Arg$^{B32}$-human insulin, $N^{\epsilon B29}$-octanoyl-$N^{\alpha B1}$-octanoyl-Gly$^{A21}$Arg$^{B31}$Arg$^{B32}$-human insulin, $N^{\epsilon B29}$-propionyl-$N^{\alpha A1}$-propionyl-Gly$^{A21}$Arg$^{B31}$Arg$^{B32}$-human insulin, $N^{\alpha A1}$-acetyl-$N^{\alpha B1}$-acetyl-Gly$^{A21}$Arg$^{B31}$Arg$^{B32}$-human insulin, $N^{\epsilon B29}$-formyl-$N^{\alpha A1}$-formyl-$N^{\alpha B1}$-formyl-Gly$^{A21}$Arg$^{B31}$Arg$^{B32}$-human insulin, $N^{\epsilon B29}$-formyl-des(B26)-human insulin, $N^{\alpha B1}$-acetyl-Asp$^{B28}$-human insulin, $N^{\epsilon B29}$-propionyl-$N^{\alpha A1}$-propionyl-$N^{\alpha B1}$-propionyl-Asp$^{B1}$Asp$^{B3}$Asp$^{B21}$-human insulin, $N^{\epsilon B29}$-pentanoyl-Gly$^{A21}$-human insulin, $N^{\alpha B1}$-hexanoyl-Gly$^{A21}$-human insulin, $N^{\alpha A1}$-heptanoyl-Gly$^{A21}$-human insulin, $N^{\epsilon B29}$-octanoyl-$N^{\alpha B1}$-octanoyl-Gly$^{A21}$-human insulin, $N^{\epsilon B29}$-propionyl-$N^{\alpha A1}$-propionyl-Gly$^{A21}$-human insulin, $N^{\alpha A1}$-acetyl-$N^{\alpha B1}$-acetyl-Gly$^{A21}$-human insulin, $N^{\epsilon B29}$-formyl-$N^{\alpha A1}$-formyl-$N^{\alpha B1}$-formyl-Gly$^{A21}$-human insulin, $N^{\epsilon B29}$-butyryl-des(B30)-human insulin, $N^{\alpha B31}$-butyryl-des(B30)-human insulin, $N^{\alpha A1}$-butyryl-des(B30)-human insulin, $N^{\epsilon B29}$-butyryl-$N^{\alpha B31}$-butyryl-des(B30)-human insulin, $N^{\epsilon B29}$-butyryl-$N^{\alpha A1}$-butyryl-des(B30)-human insulin, $N^{\alpha A1}$-butyryl-$N^{\alpha B31}$-butyryl-des(B30)-human insulin, $N^{\epsilon B29}$-butyryl-$N^{\alpha A1}$-butyryl-$N^{\alpha B31}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

As discussed in more detail below, the insulin molecule may be conjugated to the affinity ligand and/or monovalent glucose binding agent via one or more reactive moieties that are naturally present within the insulin structure or artificially added prior to conjugation (e.g., carboxyl or reactive ester, amine, hydroxyl, aldehyde, sulfhydryl, maleimidyl, alkynyl, azido, etc. moieties). For example, insulin naturally includes reactive alpha-terminal amine and epsilon-amine lysine groups. In certain embodiments, a modified insulin may be employed in which a suitable amino acid (e.g., a lysine) has been added or substituted into the amino acid sequence in order to provide an alternative point of conjugation. In addition, as discussed in more detail below, it will be appreciated that the conjugation process may be controlled by selectively blocking certain reactive moieties prior to conjugation.

In certain embodiments, the affinity ligand is covalently bound to the insulin molecule via the A1 amino acid residue. In certain embodiments the A1 amino acid residue is glycine. It is to be understood however, that the present disclosure is not limited to N-terminal conjugation and that in certain embodiments the affinity ligand can be covalently bound to the insulin molecule via a non-terminal A-chain amino acid residue. In particular, the present disclosure encompasses conjugation via the epsilon-amine group of a lysine residue present at positions A2, A3, A4 or A5 (wild-type or introduced by site-directed mutagenesis). It will be appreciated that different conjugation positions may lead to different reductions in insulin activity and that different length linkers may be used in order to facilitate non-covalent bonding with the B-chain monovalent glucose binding agent.

In certain embodiments, the monovalent glucose binding agent is covalently bound to the insulin molecule via the B1 amino acid residue. In certain embodiments the B1 amino acid residue is phenylalanine. It is to be understood however, that the present disclosure is not limited to N-terminal conjugation and that in certain embodiments the affinity ligand can be covalently bound to the insulin molecule via a non-terminal B-chain amino acid residue. In particular, the present disclosure encompasses conjugation via the epsilon-amine group of a lysine residue present at positions B2, B3, B4 or B5 (wild-type or introduced by site-directed mutagenesis). It will be appreciated that different conjugation positions may lead to different reductions in insulin activity and that different length linkers may be used in order to facilitate non-covalent bonding with the A-chain affinity ligand.

Affinity Ligand

The affinity ligand may have the same chemical structure as glucose itself or may be a chemically related species of glucose. The only requirement is that it competes with glucose for binding with the monovalent glucose binding agent. In certain embodiments, the affinities of the affinity ligand and glucose for the monovalent glucose binding agent are both in the range of 0.5 to 50 mM, e.g., 2 to 20 mM, 4 to 10 mM, etc. In certain embodiments, the affinity of the affinity ligand for the monovalent glucose binding agent is no more than 10× (e.g., no more than 1×, 5× or 10×) greater than the affinity of glucose for the monovalent glucose binding agent.

In certain embodiments, the affinity ligand is of formula (Ia) or (Ib):

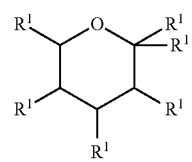

Ia

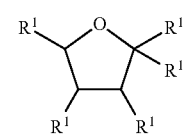

Ib wherein:
each $R^1$ is independently hydrogen, —$OR^y$, —$N(R^y)_2$, —$SR^y$, —O—Y, -G-Z, or —$CH_2R^x$;
each $R^x$ is independently hydrogen, —$OR^y$, —$N(R^y)_2$, —$SR^y$, or —O—Y;
each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by —O—, —S—, —$N(R^2)$—, —C(O)—, —OC(O)—, —C(O)O—, —C(O)N($R^2$)—, —$N(R^2)C(O)$—, —$N(R^2)C(O)N(R^2)$—, —$SO_2$—, —$SO_2N(R^2)$—, —$N(R^2)SO_2$—, or —$N(R^2)SO_2N(R^2)$—;
each Z is independently halogen, —$N(R^2)_2$, —$OR^2$, —$SR^2$, —$N_3$, —C≡$CR^2$, —$CO_2R^2$, —$C(O)R^2$, or —$OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the affinity ligand of formula (Ia) or (Ib) is a monosaccharide. In certain embodiments, the affinity ligand is a disaccharide. In certain embodiments, the affinity ligand is a trisaccharide. In certain embodiments, the affinity ligand is a tetrasaccharide. In certain embodiments, the affinity ligand comprises no more than four saccharide moieties.

As defined generally above, each $R^1$ is independently hydrogen, —$OR^y$, —$N(R^y)_2$, —$SR^y$, —O—Y, -G-Z, or —$CH_2R^x$. In certain embodiments, $R^1$ is hydrogen. In certain embodiments, $R^1$ is —OH. In other embodiments, $R^1$ is —$NHC(O)CH_3$. In certain embodiments, $R^1$ is —O—Y. In certain other embodiments, $R^1$ is -G-Z. In some embodiments, $R^1$ is —$CH_2OH$. In other embodiments, $R^1$ is —$CH_2$—O—Y. In yet other embodiments, $R^1$ is —$NH_2$. One of ordinary skill in the art will appreciate that each $R^1$ substituent in formula (Ia) or (Ib) may be of (R) or (S) stereochemistry.

As defined generally above, each Rx is independently hydrogen, —$OR^y$, —$N(R^Y)_2$, —$SR^y$, or —O—Y. In some embodiments, Rx is hydrogen. In certain embodiments, Rx is —OH. In other embodiments, $R^x$ is —O—Y.

As defined generally above, each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$. In some embodiments, $R^y$ is hydrogen. In other embodiments, $R^y$ is —$R^2$. In some embodiments, $R^y$ is —$C(O)R^2$. In certain embodiments, $R^y$ is acetyl. In other embodiments, $R^y$ is —$SO_2R^2$, —$S(O)R^2$, —$P(O)(OR^2)_2$, —$CO_2R^2$, or —$C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of —O—Y through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by —O—, —S—, —$N(R^2)$—, —C(O)—, —OC(O)—, —C(O)O—, —$C(O)N(R^2)$—, —$N(R^2)C(O)$—, —$N(R^2)C(O)N(R^2)$—, —$SO_2$—, —$SO_2N(R^2)$—, —$N(R^2)SO_2$—, or —$N(R^2)SO_2N(R^2)$—. In some embodiments, G is a covalent bond. In certain embodiments, G is —O—$C_{1-8}$ alkylene. In certain embodiments, G is —$OCH_2CH_2$—.

As defined generally above, each Z is independently halogen, —$N(R^2)_2$, —$OR^2$, —$SR^2$, —$N_3$, —C≡$CR^2$, —$CO_2R^2$, —$C(O)R^2$, or —$OSO_2R^2$. In some embodiments, Z is a halogen or —$OSO_2R^2$. In other embodiments, Z is —$N_3$ or —C≡$CR^2$. In certain embodiments, Z is —$N(R^2)_2$, —$OR^2$, or —$SR^2$. In certain embodiments, Z is —SH. In certain embodiments, Z is —$NH_2$. In certain embodiments, -G-Z is —$OCH_2CH_2NH_2$.

In some embodiments, the $R^1$ substituent on the C1 carbon of formula (Ia) is —G-Z to give a compound of formula (Ia-i):

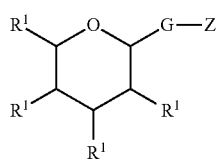

Ia-i wherein $R^1$, G, and Z are as defined and described herein.

In some embodiments, the ligand is of formula (Ia-ii):

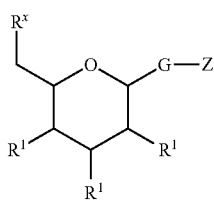

Ia-ii wherein $R^1$, $R^x$, G, and Z are as defined and described herein.

Figure 2:
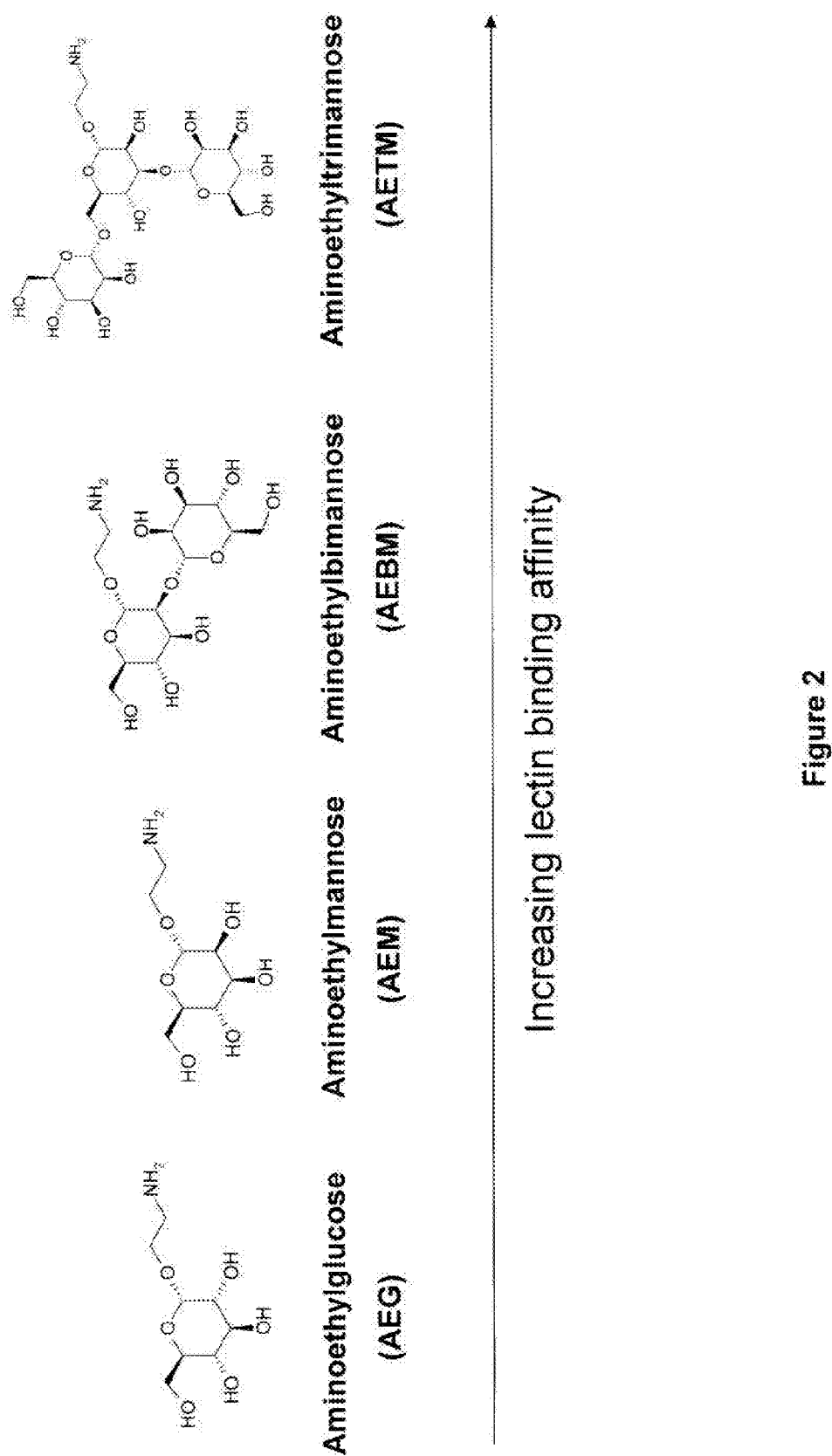
FIG. 2: shows the chemical structures of some exemplary A-chain affinity ligands (AEG, AEM, AEBM and AETM). The affinity of these sugar based affinity ligands for Con A increases as shown.

In various embodiments it may be advantageous for the affinity ligand to have a different chemical structure from glucose, e.g., in order to fine tune the relative affinity of the monovalent glucose binding agent for the affinity ligand and free glucose. For example, in various embodiments, the affinity ligand may be a saccharide or a polysaccharide. In certain embodiments the saccharide may be a natural saccharide (e.g., glucose, fructose, galactose, mannose, arabinose, ribose, xylose, etc.). In certain embodiments the saccharide may be a modified saccharide (e.g., 2'-fluororibose, 2'-deoxyribose, hexose, etc.). In certain embodiments the affinity ligand may be glucose, sucrose, maltose, mannose, derivatives of these (e.g., glucosamine, mannosamine, methylglucose, methylmannose, ethylglucose, ethylmannose, etc.) and/or higher order combinations of these (e.g., linear and/or branched bimannose, linear and/or branched trimannose, etc.). In certain embodiments, the affinity ligand is a monosaccharide. In certain embodiments, the affinity ligand is a disaccharide. In certain embodiments, the affinity ligand is a trisaccharide. In certain embodiments, the affinity ligand is a polysaccharide. In certain embodiments, the affinity ligand includes from 1-10 saccharide moieties, e.g., 1, 2, 3, 4, 5, 6, 7, 8, 9 or 10 moieties. In some embodiments, the affinity ligand comprises a saccharide and one or more amine groups. In some embodiments, the affinity ligand is aminoethylglucose (AEG). In some embodiments, the affinity ligand is aminoethylmannose (AEM). In some embodiments, the affinity ligand is aminoethylbimannose (AEBM). In some embodiments, the affinity ligand is aminoethyltrimannose (AETM). FIG. 2 shows the structures of some of these exemplary affinity ligands. In various embodiments, the affinity ligand is a polysaccharide, glycopeptide or glycolipid. Other exemplary affinity ligands will be recognized by those skilled in the art.

Methods for conjugating affinity ligands to an insulin molecule are discussed in more detail below. In certain embodiments, the affinity ligand is conjugated to the insulin molecule via the C1, C2 or C6 position of a terminal saccharide within the affinity ligand. In certain embodiments, conjugation occurs via the C1 position. The C1 position is also referred to as the anomeric carbon and may be conjugated to the insulin molecule in the alpha or beta conformation. In certain embodiments, the C1 position is conjugated as the alpha anomer.

In various embodiments, the affinity ligand for a particular conjugate may be selected empirically. According to such embodiments one or more affinity ligands are screened based on their relative binding affinities for the monovalent glucose binding agent as compared to glucose. In certain embodiments a library of saccharides and/or polysaccharides are screened in this manner. A suitable affinity ligand will exhibit a detectable level of competition with glucose but will not compete so strongly that it prevents all binding between free glucose and the monovalent glucose binding agent.

Monovalent Glucose Binding Agent

1. Polypeptides

In various embodiments, the monovalent glucose binding agent may include a polypeptide. As discussed in more detail below, suitable polypeptides can include certain monovalent lectins, peptide aptamers and antibodies (including their glucose binding fragments).

a. Lectins

In certain embodiments, monovalent glucose-binding lectins may be used. As discussed in more detail below, in certain embodiments, it may be advantageous to chemically modify the lectins. Lectins have been isolated from a variety of natural sources including seeds, roots, bark, fungi, bacteria, seaweed, sponges, mollusks, fish eggs, body fluids of invertebrates and lower vertebrates, and mammalian cell membranes (e.g., see *The Lectins: Properties, Functions, and Applications in Biology and Medicine*, Edited by Liener et al., Academic Press, 1986). A number of lectins have also been produced recombinantly (e.g., see Streicher and Sharon, *Methods Enzymol*. 363:47-77, 2003 and U.S. Patent Publication No. 2006/0247154). As noted above, lectins bind saccharides and polysaccharides with a high degree of specificity. For example, some lectins will bind only to mannose or glucose residues, while others only recognize galactose residues. Some lectins require that the particular residue be in a terminal position, while others bind to residues within a polysaccharide chain. Some lectins require specific anomeric structures and yet others recognize specific sugar sequences. The structures and properties of lectins have been extensively described in the literature. For recent reviews and a list of glucose-binding lectins see Lectins, Edited by Sharon and L is, Kluwer Academic Publishers, 2003; *Handbook of Animal Lectins: Properties and Biomedical Applications*, Edited by Kilpatrick, Wiley, 2000; and *Handbook of Plant Lectins: Properties and Biomedical Applications*, Edited by Van Damme et al., Wiley, 1998. Exemplary glucose-binding lectins include calnexin, calreticulin, N-acetylglucosamine receptor, selectin, asialoglycoprotein receptor, collectin (mannose-binding lectin), mannose receptor, aggrecan, versican, pisum sativum agglutinin (PSA), vicia faba lectin, lens culinaris lectin, soybean lectin, peanut lectin, lathyrus ochrus lectin, sainfoin lectin, sophora japonica lectin, bowringia milbraedii lectin, concanavalin A (Con A), and pokeweed mitogen. In various embodiments, human analogs of plant lectins may be used. These include, without limitation, human mannan binding protein (MBP, also called mannan binding lectin, Sheriff et al., *Structural Biology*, 1:789-794 (1994); Dumestre-Perard et al., *Molecular Immunology*, 39:465-473 (2002)), human pulmonary surfactant protein A (SP-A, Allen, et al., *Infection and Immunity*, 67:4563-4569 (1999)), human pulmonary surfactant protein D (SP-D, Persson et al., *The Journal of Biological Chemistry*, 265:5755-5760 (1990)), CL-43 (a human serum protein), and conglutinin.

Many lectins are multimeric (e.g., dimeric or tetrameric) and will need to be converted into a monomeric form for use with the present invention. For example, in certain embodiments, a monovalent monomer derivative of Con A (Mm-Con A) can be prepared as described previously (Saito et al., *J. Biol. Chem.* 256: 7499-7505, 1983 and Tanaka et al., *J. Biochem. (Tokyo)* 89: 1643-1646, 1981) by photoalkylation of Con A using chloroacetamide. This monomer preparation, which is purified to the final purification stage by affinity chromatography and gel filtration, can be demonstrated to be completely free of both dimers and tetramers by the analytical rechromatography on Sephadex G-100 and by gel filtration through a column of Bio-Gel P-100. The Mm-ConA preparation can also be shown to be completely monomeric by velocity and equilibrium sedimentation experiments. Alternatively, monomeric concanavalin A can be produced by digestion or by recombinant production of monomers (e.g., see Wands et al. in *Proc. Natl. Acad. Sci. USA* 73: 2118-2122, 1976 and WO/2006/091942). In certain embodiments, the naturally monomeric bacterial periplasmic glucose/galactose binding protein may be used. (e.g., see Ye and Schultz in *Anal. Chem.* 75: 3451-3459, 2003; Vyas et al. in *Biochemistry* 33: 4762-4768, 1994; and Marvin et al. in *Proc. Natl. Acad. Sci. USA* 94: 4366-4371, 1997)

b. Peptide Aptamers

In certain embodiments monovalent peptide aptamers may be used. As is well known in the art, peptide aptamers consist of a variable ligand-binding peptide loop fused within a protein scaffold (e.g., see Hoppe-Seyler and Butz, *J. Mol. Med.* 78:426-430, 2000 and Crawford et al., *Briefings in Functional Genomics and Proteomics* 2:72-79, 2003). The variable loop typically includes between about 10 and 20 amino acids. A variety of scaffold proteins may be used. In general, the site of insertion is chosen such that the peptide loop disrupts a region of the scaffold that would otherwise mediate some wild-type function, e.g., the bacterial protein thioredoxin-A in which the variable loop is inserted within the reducing active site (a -Cys-Gly-Pro-Cys- loop in the wild-type protein). Peptide aptamers with suitable affinity for glucose can be prepared and selected using any known method. For example, yeast two-hybrid libraries, yeast expression libraries, bacterial expression libraries and/or retroviral libraries for expression in mammalian cells may be used.

In various embodiments, peptide aptamers may be selected by affinity chromatography. According to such embodiments, peptide aptamers in a library are exposed to glucose and those that do not bind glucose are removed. The bound peptide aptamers are then eluted and cloned for subsequent rounds of selection. A new library is then generated from one or more of these peptide aptamers (e.g., the peptide aptamer with the highest affinity for glucose in the first round of selection) and the stringency of the elution conditions is increased or modified to identify peptide aptamers with the desired binding affinity and/or specificity. In various embodiments, the selection process may involve steps in which the stringency of the elution conditions are gradually increased in order to select peptide aptamers with high affinity for glucose. In various embodiments, the selection process may involve steps in which the elution conditions are modified (e.g., by using a different affinity column) in order to select peptide aptamers with desired specificity for glucose. In various embodiments the selection process may generate a collection of sublibraries (or "pools") each of which comprises peptide aptamers with similar affinities and/or specificities for glucose. In various embodiments the selection process may generate a single peptide aptamer sequence (or "monoclonal"). It will be appreciated that any of these peptide aptamer sequences may be cloned for future recombinant expression.

2. Polynucleotides

In various embodiments, the monovalent glucose binding agent may include a polynucleotide aptamer. In general, monovalent aptamers will first be generated based on their binding properties for glucose. As is well known in the art, aptamers to glucose can be generated through a process of in vitro selection. See Ellington and Szostak (1990) Nature 346: 818; Tuerk and Gold (1990) Science 249:505; and U.S. Pat. No. 5,582,981.

Typically, the process begins with the synthesis of a library consisting of randomly generated polynucleotide sequences of fixed length flanked by constant 5' and 3' ends that serve as primers. In certain embodiments (e.g., when optimizing an aptamer) one might start with a sequence which is known to bind glucose and generate a library which includes a collection of polynucleotides which exhibit a limited range of changes from the starting sequence (e.g., a random set of single mutations). The sequences in the library are then exposed to glucose and those that do not bind glucose are removed (e.g., by affinity chromatography). The bound sequences are then eluted and amplified (e.g., by cloning and subsequent transcription or by PCR) to prepare for subsequent rounds of selection in which the stringency of the elution conditions is increased or modified to identify sequences with the desired binding affinity and/or specificity. Jarosch et al., *Nucleic Acids Res.* 34:86, 2006 have described methods that allow the process to be performed without the constant primer regions.

In various embodiments, the selection process may involve steps in which the stringency of the elution conditions are gradually increased in order to select aptamers with high affinity for glucose.

In various embodiments, the selection process may involve steps in which the elution conditions are modified (e.g., by using a different affinity column) in order to select aptamers with desired specificity for glucose.

In various embodiments the selection process may generate a collection of sublibraries (or "pools") each of which comprises aptamers with similar affinities and/or specificities for glucose. In various embodiments the selection process may generate a single aptamer sequence (or "monoclonal"). In various embodiments the aptamers are DNA based. In various embodiments the aptamers are RNA based. In various embodiments the aptamers are mixed RNA/DNA aptamers.

Figure 3:
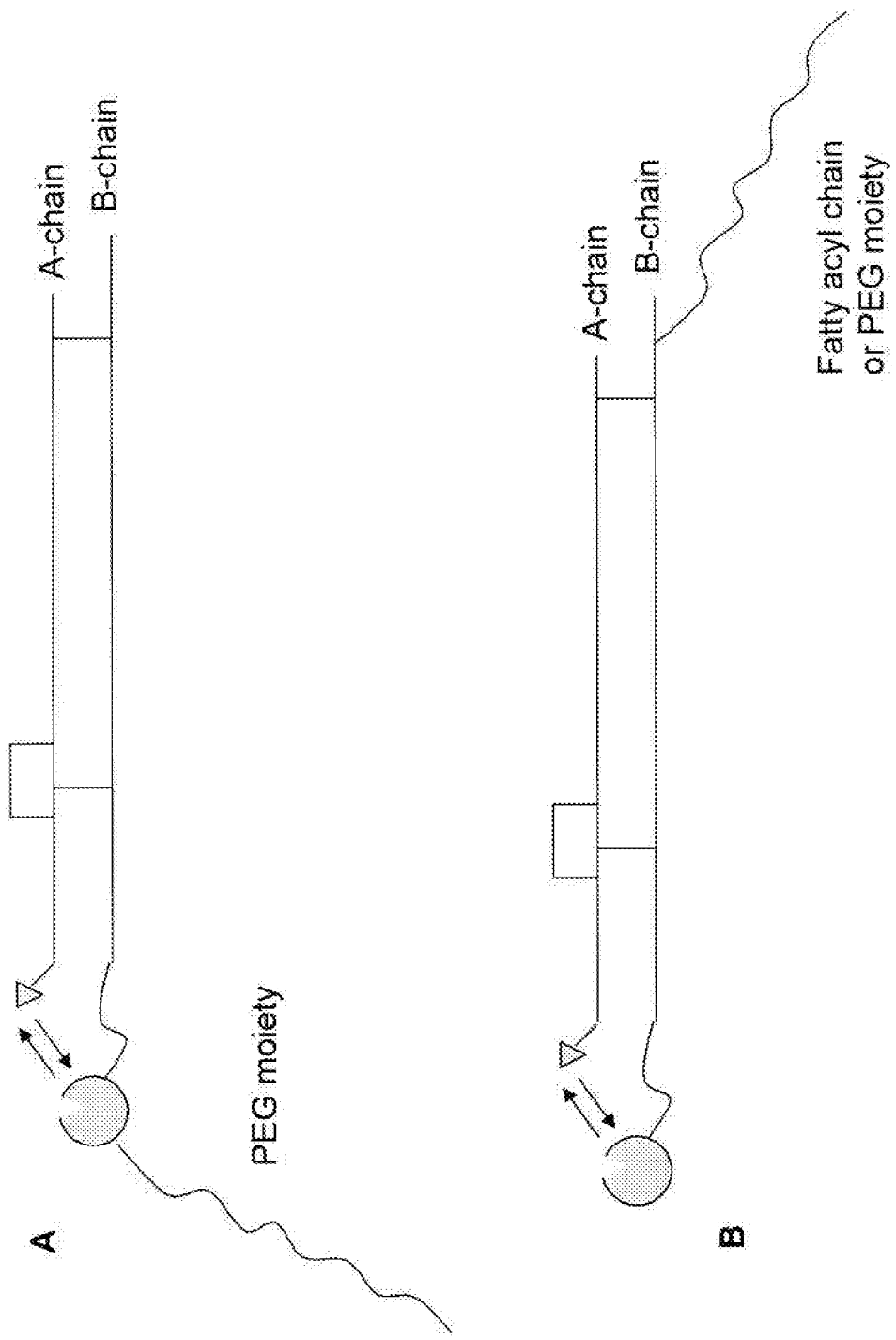
FIG. 3: shows some alternative embodiments of an inventive conjugate.

In various embodiments, a polynucleotide aptamer of the present disclosure binds glucose and includes at least 40, 50, 60, 70 or 80 contiguous nucleotides of SEQ ID NO. 1, 2, 3, 4, 5, 6 or 7 (see FIG. 3). In various embodiments, an aptamer of the present disclosure binds glucose and comprises a region having at least 70% homology with at least 40, 50, 60, 70 or 80 contiguous nucleotides of SEQ ID NO. 1, 2, 3, 4, 5, 6 or 7. In various embodiments, an aptamer of the present disclosure binds glucose and comprises a region having at least 80% homology with at least 40, 50, 60, 70 or 80 contiguous nucleotides of SEQ ID NO. 1, 2, 3, 4, 5, 6 or 7. In various embodiments, an aptamer of the present disclosure binds glucose and comprises a region having at least 90% homology with at least 40, 50, 60, 70 or 80 contiguous nucleotides of SEQ ID NO. 1, 2, 3, 4, 5, 6 or 7. In various embodiments, an aptamer of the present disclosure binds glucose and comprises a region having at least 95% homology with at least 40, 50, 60, 70 or 80 contiguous nucleotides of SEQ ID NO. 1, 2, 3, 4, 5, 6 or 7.

In various embodiments, an aptamer of the present disclosure binds glucose and includes a nucleotide sequence of SEQ ID NO. 8, 9 or 10:

| SEQUENCE[1] | SEQ ID NO. |
|---|---|
| NNANCYGCGNGNNANCYYCARNCANNAA CAGNACACNNAA | 8 |
| NACAGNACGGGGNGANCACCAANGCNG AANGCAGAAGCG | 9 |
| GNCAGGANAGGNGCAAGAANGCGAAANN CGCAGGCNGGNG | 10 |

[1]N = U/T; Y = U/T or C; R = A or G

SEQ ID NO. 8 is a consensus sequence based on the central (i.e., non-primer) regions of SEQ ID NOs. 2, 3, 5, 7 (see FIG. 5). SEQ ID NO. 9 is based on the central region of SEQ ID NO. 4. SEQ ID NO. 10 is based on the central region of SEQ ID NO. 6.

In certain embodiments, the nucleotide sequence is an RNA sequence and N=U. In certain embodiments, the nucleotide sequence is a DNA sequence and N=T.

In certain embodiments, an aptamer of the present disclosure binds glucose and includes a nucleotide sequence of SEQ ID NO. 8 wherein Y=U/T. In certain embodiments, an aptamer of the present disclosure binds glucose and includes a nucleotide sequence of SEQ ID NO. 8 wherein Y=C. In certain embodiments, an aptamer of the present disclosure binds glucose and includes a nucleotide sequence of SEQ ID NO. 8 wherein Y(6)=U/T and Y(17-18)=C. In certain embodiments, an aptamer of the present disclosure binds glucose and includes a nucleotide sequence of SEQ ID NO. 8 wherein R=A. In certain embodiments, an aptamer of the present disclosure binds glucose and includes a nucleotide sequence of SEQ ID NO. 8 wherein R=G.

In various embodiments, an aptamer of the present disclosure binds glucose and comprises a region having at least 70% homology with at least 30 contiguous nucleotides of SEQ ID NO. 8, 9 or 10. In various embodiments, an aptamer of the present disclosure binds glucose and comprises a region having at least 80% homology with at least 30 contiguous nucleotides of SEQ ID NO. 8, 9 or 10. In various embodiments, an aptamer of the present disclosure binds glucose and comprises a region having at least 90% homology with at least 30 contiguous nucleotides of SEQ ID NO. 8, 9 or 10. In various embodiments, an aptamer of the present disclosure binds glucose and comprises a region having at least 95% homology with at least 30 contiguous nucleotides of SEQ ID NO. 8, 9 or 10.

In various embodiments, an aptamer of the present disclosure binds glucose and comprises a region having at least 70% homology with SEQ ID NO. 8, 9 or 10. In various embodiments, an aptamer of the present disclosure binds glucose and comprises a region having at least 80% homology with SEQ ID NO. 8, 9 or 10. In various embodiments, an aptamer of the present disclosure binds glucose and comprises a region having at least 90% homology with SEQ ID NO. 8, 9 or 10. In various embodiments, an aptamer of the present disclosure binds glucose and comprises a region having at least 95% homology with SEQ ID NO. 8, 9 or 10.

In various embodiments, the present disclosure provides a pool of monovalent aptamers that bind glucose and each independently comprise a region having at least 70% homology with at least 30 contiguous nucleotides of SEQ ID NO. 8, 9 or 10. In various embodiments, the present disclosure provides a pool of monovalent aptamers that bind glucose and each independently comprise a region having at least 80% homology with at least 30 contiguous nucleotides of SEQ ID NO. 8, 9 or 10. In various embodiments, the present disclosure provides a pool of monovalent aptamers that bind glucose and each independently comprise a region having at least 90% homology with at least 30 contiguous nucleotides of SEQ ID NO. 8, 9 or 10. In various embodiments, the present disclosure provides a pool of monovalent aptamers that bind glucose and each independently comprise a region having at least 95% homology with at least 30 contiguous nucleotides of SEQ ID NO. 8, 9 or 10. In certain embodiments, the pool includes more than 10, more than 20, more than 50 or more than 100 monovalent aptamers.

In various embodiments, the present disclosure provides a pool of monovalent aptamers that bind glucose and each independently comprise a region having at least 70% homology with SEQ ID NO. 8, 9 or 10. In various embodiments, the present disclosure provides a pool of monovalent aptamers that bind glucose and each independently comprise a region having at least 80% homology with SEQ ID NO. 8, 9 or 10. In various embodiments, the present disclosure provides a pool of monovalent aptamers that bind glucose and each independently comprise a region having at least 90% homology with SEQ ID NO. 8, 9 or 10. In various embodiments, the present disclosure provides a pool of monovalent aptamers that bind glucose and each independently comprise a region having at least 95% homology with SEQ ID NO. 8, 9 or 10. In certain embodiments, the pool includes more than 10, more than 20, more than 50 or more than 100 monovalent aptamers.

3. Chemical Modification of Monovalent Glucose Binding Agent

In general, it is to be understood that any of the aforementioned monovalent glucose binding agents may be chemically modified, e.g., as illustrated in FIG. 3A, in certain embodiments it may be advantageous to chemically modify (e.g., pegylate) the monovalent glucose binding agent in order to produce a long-circulating construct.

In US 2007-0110811 we described the benefits of chemically modifying multivalent lectins (e.g., by pegylation) in order to reduce their in vivo mitogenicity. However, chemical modifications such as pegylation can also be used to slow clearance. Thus, in certain embodiments, monovalent glucose binding agent may be covalently modified with one or more compounds. Wihout limitation this might involve reaction with an activated pegylation (PEG) agent (e.g., without limitation N-hydroxysuccinimide activated PEG, succinimidyl ester of PEG propionic acid, succinimidyl ester of PEG butanoic acid, succinimidyl ester of PEG alpha-methylbutanoate, etc.), another water soluble but non-PEG-containing polymer such as poly(vinyl alcohol), a reagent that can be easily coupled to lysines, e.g., through the use of carbodiimide reagents, a perfluorinated compound, etc. The skilled artisan will readily recognize other suitable compounds, e.g., by referring to the comprehensive review that can be found in *Chemical Reagents for Protein Modification* by Lundblad, CRC Press, 3$^{rd}$ Edition, 2004.

In general, the compound(s) may be attached to a monovalent glucose binding agent (e.g., a monovalent lectin or aptamer) via any of a number of attachment methods known to those skilled in the art (e.g., via amine, carboxyl, hydroxyl or sulfhydryl groups). The potential covalent linkages are similarly diverse (e.g., including amide bonds, carbamate bonds, ester bonds, thioether bonds, ether bonds, disulfide bonds, etc.). For example, PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs (or other compounds). In preferred embodiments PEGs are covalently attached to an amino group, especially the free amino group found in lysine residues.

Numerous methods for directly attaching PEGs to polypeptides are described in Delgado et al., *Crit. Rev. Thera. Drug Carrier Sys.* 9:249-304, 1992; Francis et al., *Intern. J. of Hematol.* 68:1-18, 1998; U.S. Pat. No. 4,002,531; U.S. Pat. No. 5,349,052; WO 95/06058; and WO 98/32466. One such method uses tresylated monomethoxy poly(ethylene glycol) (MPEG), which is produced by reacting MPEG with tresylchloride ($ClSO_2CH_2CF_3$). Tresylated MPEG reacts with exposed amine groups on lectins. A skilled person will recognize that the invention is not limited to any specific pegylation agent (or compound) and will be able to identify other suitable compounds that are known in the art.

In certain embodiments PEGs (or other compounds) may be attached to a monovalent glucose binding agent via an intervening linker. For example, U.S. Pat. No. 5,612,460, discloses urethane linkers for connecting PEG to polypeptides. PEGs can be attached to a polypeptide via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional PEG derivatives and reaction chemistries for attaching PEG to polypeptides are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogues can be obtained from these commercial PEG suppliers that describe a range of suitable PEG compounds and chemistries (e.g., see the Nektar Advanced PEGylation CATALOG 2004).

In various embodiments, N-terminal alpha-amine and/or epsilon-amino lysine groups of polypeptide based monovalent glucose binding agent may be succinylated and/or acetylated to change the charge distribution as well as any tertiary and quaternary effects associated with such changes. For example, polypeptides may be succinylated by reaction in a saturated sodium acetate buffer with an excess of succinic anhydride. Acetylation may be performed using the same procedure but with acetic anhydride as the modifying agent. For example, when the monovalent glucose binding agent is derived from concanavalin A, both acetylation and succinylation not only increase the density of negative charge within the polypeptide but also reduce the formation of tetramers at physiological pH (e.g., see Agrawal et al., *Biochemistry.* 7:4211-4218, 1968 and Gunther et al., *Proc. Natl. Acad. Sci.* (*USA*) 70:1012-1016, 1973).

In general, the number of compounds that are attached to each monovalent glucose binding agent (i.e., the degree of substitution) will vary based on the nature of the monovalent glucose binding agent, the nature of the compound(s), the number of reaction sites available and the reaction conditions. For example, the subunits of concanavalin A each include twelve lysine residues. As a result, if concanavalin A is pegylated with a compound that reacts with lysine residues, then each subunit could be covalently linked to 1, 2, 3, 4, 5, 6, 7, 8, 9, 10, 11 or 12 of these compounds. Methods for determining the degree of substitution are discussed in Delgado et al., *Crit. Rev. Thera. Drug Carrier Sys.* 9:249-304, 1992. In certain embodiments, a monomeric Con A with 11 pegylated lysines may be used (where the remaining free lysine is used for conjugation to insulin).

In preferred embodiments, the chemical modification of a monovalent glucose binding agent may be optimized using a plurality of compounds and a plurality of reaction conditions (e.g., that vary the reagent concentrations, pH, temperature, etc.). For example, an automated robotic handling device may be used to prepare a range of modified compositions with different compounds and different reaction conditions. Using routine orthogonal experimentation a skilled person can then screen the properties of the treated compositions. In certain embodiments further rounds of orthogonal optimization are performed around the preferred conditions to further refine the preferred compounds and reaction conditions.

In one embodiment, optimal reaction conditions are identified by separating treated compositions by electrophoresis, preferably by denaturing SDS-PAGE electrophoresis. In various embodiments, compositions which include uniformly modified monovalent glucose binding agents are preferred. These preferred compositions will have weaker bands at the molecular weight of the unmodified monovalent glucose binding agent as measured by SDS-PAGE.

4. Purification of Monovalent Glucose Binding Agent

In various embodiments, monovalent glucose binding agents (whether they have been chemically modified or not) can be further processed in order to improve their properties. Thus, in certain embodiments, compositions comprising monovalent glucose binding agents can be purified in order to remove protein fragments, unmodified components, etc. In general, these separations can be achieved on the basis of physical properties (e.g., electrical charge; molecular weight; and/or size) and/or chemical properties (e.g., binding affinity for a target molecule). In certain embodiments optimal removal may be achieved by combining two or more methods that rely on these differential properties. In one embodiment, these separations are performed under denaturing conditions. For example, unmodified or partially modified monovalent glucose binding agents can be removed on the basis of their net charge by ion-exchange chromatography. Gel-filtration chromatography may be used to discriminate between differentially modified monovalent glucose binding agents on the basis of size. Affinity chromatography is another method that may be used to remove unmodified or partially modified monovalent glucose binding agents. This approach takes advantage of the differential binding affinity of modified, partially modified and unmodified monovalent glucose binding agents for glucose.

Conjugation to Insulin

In general, the affinity ligand and monovalent glucose binding agent (each generally referred to in this section as a "component") are covalently bound to the insulin. Components can be directly bonded (i.e., with no intervening chemical groups) or indirectly bonded through a spacer (e.g., a coupling agent or covalent chain that provides some physical separation between the conjugated element and the insulin). It is to be understood that components may be covalently bound to an insulin through any number of chemical bonds, including but not limited to amide, amine, ester, ether, thioether, isourea, imine, etc. bonds. In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to an insulin via natural or chemically added pendant groups. In general, it will be appreciated that the first and second members of a pair of reactive groups (e.g., a carboxyl group and an amine group which react to produce an amide bond) can be present on either one of the component and insulin (i.e., the relative location of the two members is irrelevant as long as they react to produce a conjugate). Exemplary linkages are discussed in more detail below.

1. A-Chain Affinity Ligand

In certain embodiments, the affinity ligand may be covalently bonded to the $NH_2$-terminus of the A1 amino acid residue (Gly in wild-type human insulin) according to the following non-limiting exemplary procedure:

i. Preparation of $NH_2$-A1-di-MSC-(B1, B29)-insulin

Insulin is protected at the B1 and B29 amines according to the procedure described in Li et al., *IUBMB Life*, 53:57-60, 2002 by first reacting the A1 terminus with Boc-azide in 80% pyridine followed by ion-exchange chromatography to isolate the N-A1-Boc-insulin product. The B1 and B29 groups are subsequently blocked with MSC groups by reacting the N-A1-Boc-insulin with methylsulfonylethoxycarbonyl N-succinimidyl ester (Msc-ONSu) in DMSO. After superdilution of the product in water followed by size exclusion chromatography on a Biogel P2 column, the N-A1-Boc-(B1, B29-MSC2)-insulin product is lyophilized. Finally, the Boc group is removed by trifluoracetic acid/anisole treatment, superdiluted in water, purified by exclusion chromatography on a Biogel P2 column, and lyophilized to obtain the pure $NH_2$-A1-di-MSC-(B1, B29)-insulin.

ii. Reaction of $NH_2$-A1-di-MSC-(B1, B29)-insulin with Amino-Functionalized Affinity Ligands and Subsequent Deprotection As described in the Examples, we have exemplified methods for preparing the insulin substituted at the A-chain with aminoethylglucose (AEG), aminoethylmannose (AEM), aminoethylbimannose (AEBM), and/or aminoethyltrimannose (AETM) as exemplary affinity ligands. Without limitation, di-activated esters are useful reagents for coupling both the $NH_2$-A1 terminus of insulin with the amino groups on the AEG, AEM, AEBM, and AETM sugars. Exemplary di-activated esters include bis[2-(Succinimidooxycarbonyloxy)ethyl]sulfone (BSOCOES), Succinimidyloxycarbonyl-b-alanine-hydroxysuccinimide ester, Disuccinimidyl-L-tartrate (DST), Di-sulfo-succinimidyl-L-tartrate, Disuccinimidyl suberate (DSS), Disuccinimidyl sebacate, Disuccinimidyl dodecanoate (DSD), Hexadecanediol-bis-succinimidyl carbonate, and bis-sulfo-succinimidyl suberate (BS3) all of which may be purchased from Molecular Biosciences (Boulder, Colo.). The spacing distance between the insulin and affinity ligand may be controlled via the proper choice of di-activated ester.

For example, for purposes of illustration, in one embodiment, both the affinity ligand (e.g., AEG, AEM, AEMB and AETM) and $NH_2$-A1-di-MSC-(B1, B29)-insulin may be reacted to a DSS framework through the terminal activated esters to produce insulin-DSS-AEG, insulin-DSS-AEM, insulin-DSS-AEMB, and insulin-DSS-AETM conjugates. The various affinity ligands are synthesized ahead of time as discussed in the Examples. Approximately one equivalent of $NH_2$-A1-di-MSC-(B1, B29)-insulin as a 40-50 mg/ml solution in DMSO is added at room temperature to a 50 mg/ml solution of DSS in DMSO containing excess triethylamine and allowed to react for approximately one hour. Next, an excess of AEG, AEM, AEBM, or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted $BOC_2$-insulin. The desired elution peak is collected pooled and rotovapped to remove acetonitrile followed by lyophilization to obtain a dry powder. Finally, the MSC protecting groups are removed by dissolving the lyophilized powder in 2N NaOH at 0° C. for 5 minutes followed by rapid neutralization with glacial acetic acid to pH 7 and 10× superdilution in HEPES pH 8.2 buffer containing 0.150M NaCl. The resulting solution is passed through a Biogel P2 column to remove impurities and eluted into DI water. The deprotected, purified aqueous conjugate solution is then lyophilized until needed.

2. B-Chain Monovalent Glucose Binding Agent Coupling to A-Chain-Affinity Ligand-Modified Insulin In certain embodiments, the monovalent glucose binding agent may be bound to the B1 amino acid residue of insulin (Phe in wild-type human insulin) according to the following exemplary method. First, the B29 epsilon amino group of the A-chain-affinity ligand-modified insulin (AAMI) is protected with BOC as described in the Examples section. Briefly, the AAMI is dissolved in DMSO containing excess equivalents of triethylamine (TEA) followed by the slow addition of 1.3 equivalents of di-tert-butyl-dicarbonate (THF solution)

(Sigma Aldrich, St. Louis, Mo.). The reaction is quenched via the addition of ethanolamine and the entire solution poured into 1600 ml of acetone and mixed briefly with a spatula. After precipitating the material with HCl, the product is centrifuged and washed exhaustively with acetone and dried to obtain the crude powder. The desired B29-BOC1 product can then be isolated via preparative RP-HPLC followed by lyophilization to obtain the pure powder.

Next, an amino-functionalized diethyl acetal-containing moiety is coupled to the $NH_2$-B1 terminus using one of the di-activated esters described above (e.g. bis[2-(Succinimidooxycarbonyloxy)ethyl]sulfone (BSOCOES), Succinimidyloxycarbonyl-b-alanine-hydroxysuccinimide ester, Disuccinimidyl-L-tartrate (DST), Di-sulfo-succinimidyl-L-tartrate, Disuccinimidyl suberate (DSS), Disuccinimidyl sebacate, Disuccinimidyl dodecanoate (DSD), Hexadecanediol-bis-succinimidyl carbonate, and bis-sulfo-succinimidyl suberate (BS3) all of which may be purchased from Molecular Biosciences (Boulder, Colo.). The spacing distance between the insulin and glucose-binding agent may be controlled via the proper choice of di-activated ester.

For example, for purposes of illustration, in one embodiment, aminobutyraldehyde diethyl acetal (ABDA) and the BOC-B29-AAMI may be reacted to a DSS framework through the terminal activated esters to produce AAMI-B1-DSS-ABDA. Approximately one equivalent of the BOC-B29-AAMI as a 40-50 mg/ml solution in DMSO is added at room temperature to a 50 mg/ml solution of DSS in DMSO containing excess triethylamine and allowed to react for approximately one hour. Next, an excess of ABDA (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted $BOC_2$-insulin. The desired elution peak is collected pooled and rotovapped to remove acetonitrile followed by lyophilization to obtain a dry powder. Finally, the diethyl acetal and BOC protecting groups are removed by dissolving the lyophilized powder in a 90% TFA/10% anisole solution for one hour at 4 C followed by 10× superdilution in HEPES pH 8.2 buffer containing 0.150M NaCl and subsequent pH adjustment to 6.5. The resulting solution is passed through a Biogel P2 column to remove impurities and eluted into pH 6.5 HEPES buffered saline. Finally, the resulting aqueous conjugate solution may be concentrated to the desired level using Amicon 3K centrifugal membrane filters.

The resulting conjugate now contains an A1-substituted affinity ligand and a B1-reactive aldehyde group which may then be reacted with any amine-containing glucose binding molecule. For example, a 5× molar excess of glucose-binding molecule dissolved in a pH 6.5 buffered saline is added to a 5 mg/ml solution of the conjugate. Separately, a stock solution of reducing agent is prepared by dissolving 1.5 g of sodium cyanoborohydride (Sigma Aldrich, St. Louis, Mo.) in 15 ml of a 20 mM HEPES pH 7.0 buffer containing 0.150 M NaCl and the pH carefully adjusted to 6.5 with dilute HCl solution. Enough cyanoborohydride stock solution is added to the conjugate-glucose binding molecule solution to achieve a final concentration of 12.5 mg/ml. The resulting solution is then allowed to react overnight at room temperature. The resulting aqueous solution is then purified by size exclusion using an appropriate solid phase for the desired separation of conjugated and unconjugated glucose-binding molecules. Once collected, the solution can be dialyzed against DI water and lyophilized until further needed.

In some cases, it may be desirable to produce a conjugate that possesses increased circulation times in serum to prolong the duration of action. One non-limiting means for accomplishing this is to pre-react the glucoe-binding molecule with one or more polyethylene glycol (PEG) groups of sufficient size in such a way as to still leave at least one react amine group on the PEGylated glucose-binding molecule. The pre-PEGylated amine-reactive GBM may then be substituted in the procedure above to produce a long-circulating construct.

3. Assays

Once prepared, a conjugate can be used for a variety of applications. In general, the activation properties of a conjugate will depend on the nature of the monovalent glucose binding agent and affinity ligand. If the affinity of the glucose binding agent for the affinity ligand is much greater than for glucose then the conjugate will only activate at high concentrations of glucose. As the relative affinity of the glucose binding agent for the affinity ligand is decreased, activation will occur at lower glucose concentrations. The activation properties of the conjugate can also be adjusted by varying the composition and length of any spacer(s) present between the affinity ligand and/or glucose binding agent and the insulin. It will be appreciated that, depending on the application, these variables will enable one to produce conjugates which respond to a wide variety of glucose concentrations.

To test the bioactivity of the resulting conjugates as a function of glucose concentration, the following glucose clamp method may be used. Double jugular vein (JV/JV) catheterized rats are maintained at a desired target glucose value (100, 200, 300 or 400 mg/dl) for extended periods of time by infusing a 50% dextrose solution through the catheter line. In this type of experiment two key parameters are followed: (a) the target blood glucose level which is set by design and maintained at a particular level by adjusting (b) the glucose infusion rate (GIR). After the conjugate is injected subcutaneously at a given dose (U/kg), the GIR is adjusted to compensate for the glucose-lowering activity of the conjugate. Blood glucose levels are sampled frequently via tail vein bleeding and the glucose infusion rate (GIR) varied to compensate for any drift. The GIR required to maintain the glucose levels at a given target concentration therefore measures the activity of the conjugate at that given glucose concentration. The higher the GIR, the higher the conjugate activity. The same experiments are performed on rats receiving just a saline injection to determine the background GIR levels for each desired target glucose level. The increase in GIR following injection of the conjugate over these baseline levels can then be plotted as a function of target glucose concentration. The same experiments are also performed using an unconjugated version of the insulin molecule and the increase in GIR following injection of the unconjugated version over the baseline levels can then be plotted as a function of target glucose concentration. In certain embodiments, conjugates of the present disclosure will have lower GIR requirements at a target glucose concentration of 100 mg/dl compared to an unconjugated version of the insulin molecule and substantially the same GIR requirements at target glucose concentrations of 200, 300, and/or 400 mg/dl.

Thus in certain embodiments, in a glucose clamp rat assay performed at 100 mg/dl glucose, a conjugate may have a lower glucose infusion rate (GIR) requirement than an unconjugated version of the insulin molecule. In certain embodiments, the GIR requirement for the conjugate is at least 2× lower than for an unconjugated version of the insulin molecule. In certain embodiments, the GIR requirement for the conjugate is at least 5× lower. In certain embodiments, the GIR requirement for the conjugate is at least 10× lower. In certain embodiments, the GIR requirement for the conjugate is at least 100× lower.

In certain embodiments, in a glucose clamp rat assay performed at 200 mg/dl glucose, the conjugate has substantially the same GIR requirement as an unconjugated version of the insulin molecule. In certain embodiments, in a glucose clamp rat assay performed at 300 mg/dl glucose, the conjugate has substantially the same GIR requirement as an unconjugated version of the insulin molecule. In certain embodiments, in a glucose clamp rat assay performed at 400 mg/dl glucose, the conjugate has substantially the same GIR requirement as an unconjugated version of the insulin molecule.

In certain embodiments, in a glucose clamp rat assay performed at 200 mg/dl, the glucose infusion rate (GIR) requirement for the conjugate is within 30% of the GIR requirement for an unconjugated version of the insulin molecule. In certain embodiments, the GIR requirement is within 25, 10, 15, 10 or 5% of the GIR requirement for an unconjugated version of the insulin molecule.

In certain embodiments, in a glucose clamp rat assay performed at 300 mg/dl, the glucose infusion rate (GIR) requirement for the conjugate is within 30% of the GIR requirement for an unconjugated version of the insulin molecule. In certain embodiments, the GIR requirement is within 25, 10, 15, 10 or 5% of the GIR requirement for an unconjugated version of the insulin molecule.

In certain embodiments, in a glucose clamp rat assay performed at 400 mg/dl, the glucose infusion rate (GIR) requirement for the conjugate is within 30% of the GIR requirement for an unconjugated version of the insulin molecule. In certain embodiments, the GIR requirement is within 25, 10, 15, 10 or 5% of the GIR requirement for an unconjugated version of the insulin molecule.

In various embodiments, the conjugate is inactive when placed in pH 7 HEPES buffered saline at 37 C (50 mM HEPES, 100 mM NaCl, with 1 mM $MgCl_2$ adjusted to pH 7 with small amounts of NaOH or HCl). As is well known in the art, the activity of insulin can be assayed in vitro. One such method, the isolated fat cell assay, requires that fat cells be isolated or obtained commercially from the species of interest. The cells are incubated at low concentrations with $2$-$^3$H-glucose and increasing concentrations of unconjugated insulin or conjugated insulin. After a pre-determined incubation time, the total lipids are extracted by addition of scintillation fluid directly to the incubation vial and counted to determine the extent of incorporation of $2$-$^3$H-glucose into the lipids. In this manner, the complete dose-response curves are carried out on both the conjugated and unconjugated insulin molecule. The concentration of the conjugtaed insulin (in mole/l) required to cause half of the maximal effect is then divided into the concentration of unconjugated insulin (in mole/l) required to cause half of the maximal effect in order to obtain potency as a % of an unconjugated version of the insulin molecule.

In various embodiments, the conjugate remains substantially inactive when glucose is added to the buffer up to a threshold concentration. Above this threshold, the conjugate exhibits an increase in activity. It will be appreciated that this transition may occur sharply or may occur gradually over a range of concentrations around the threshold. In general, the desired threshold and transition will depend on the intended application for the conjugate. In particular, the desired threshold may be determined based on the normal physiological range of concentrations of glucose (which may encompass fluctuations resulting from external factors such as feeding). The normal physiological range of glucose concentrations in humans is 60 to 200 mg/dL. Glucose concentrations below 60 mg/dL are considered hypoglycemic. Glucose concentrations above 200 mg/dL are considered hyperglycemic. In various embodiments, a conjugate of the present disclosure may remain substantially inactive when placed in pH 7 HEPES buffered saline containing 20, 30, 40, 50, 60, 70, 80, 90, or 100 mg/dL glucose at 37 C. In various embodiments, the conjugate exhibits less than 1, 2, 4, 6, 8, or 10% of the activity of an unconjugated version of the insulin molecule when placed in these conditions. In various embodiments, the conjugate exhibits at least 10, 20, 30, 40, 50, 60, 70, 80, 90 or 100% of the activity of an unconjugated version of the insulin molecule when placed in pH 7 HEPES buffered saline with 100, 150, 200, 250, 300, 350 or 400 mg/dL glucose at 37 C.

It will be appreciated that the desired threshold can be readily determined for a variety of different applications. It will also be appreciated that the threshold may need to be adjusted for certain patients (e.g., based on patient gender, patients with abnormally low or high levels of glucose, etc.) or applications (e.g., a conjugate designed to activate on a more frequent basis may require a lower threshold concentration than a conjugate designed to activate less frequently).

It will be appreciated that a conjugate having a desired threshold may be generated via routine experimentation using the materials and methods described herein. For example, the same monovalent glucose binding agent can be combined with different affinity ligands can be combined to produce a series of conjugates with a gradually increasing affinity between the components of the conjugate. These conjugates will cover a spectrum of glucose thresholds. Once a lead conjugate with a suitable threshold has been identified the process can be repeated with a finer resolution to yield an optimized conjugate. Alternatively (or additionally) the same affinity ligand can be combined with a plurality of different glucose binding agents (e.g., different aptamers) that have gradually increasing affinities for the affinity ligand. This will yield a plurality of conjugates with a spectrum of thresholds that can be further refined (e.g., by varying the length and/or composition of an affinity ligand linker).

Other Conjugates

While the foregoing describes conjugates that are activated by an increase in endogenous glucose concentration, the conjugates of the present disclosure are in no way limited to glucose responsive systems. In particular, it is to be understood that conjugates can be made that are activated by saccharides other than glucose, including exogenous saccharides. In particular, a number of saccharides are known that bind Con A with higher affinity than glucose. Without limitation these include, mannose, alpha-methyl mannose, L-fucose, bimannose, methylbimannose, ethylbimmanose, trimannose, methyltrimannose, ethyltrimmanose, amino derivatives thereof, etc. Goldstein et al. provide a review of a number of Con A inhibitors and their relative affinities in *J. Biol. Chem.* 243: 2003-2007, 1968 and *Biochemistry.* 4: 876-883, 1965. Similarly, it is to be understood that other exogenous saccharides (and derivatives thereof) could be used with monovalent binding agents (e.g., other lectins, aptamers, etc.) that recognize saccharides other than glucose or mannose. In fact, in certain embodiments, it may be advantageous to use a monovalent binding agent that does not bind endogenous glucose. Exemplary lectins that do not bind glucose include those isolated from monocot plants such as *Galanthus nivalis, Allium sativum*, and *Allium ursinum*. As discussed below, one could also use aptamers that have been selected for their lack of glucose binding. Either of these approaches would reduce the risk of activation by fluctuations in endogenous levels of glucose. In various embodiments, this approach can be extended so as to avoid release in the presence of other endogenous molecules, e.g., other metabolites such as creatinine, urea, etc. In various embodiments, a conjugate may be activated by both endogenous glucose and an exogenous saccharide (e.g., mannose, alpha-methyl mannose, L-fucose, bimannose, methylbimannose, ethylbimmanose, trimannose, methyltrimannose, ethyltrimmanose, etc.). According to such embodiments background glucose activation may be supplemented by administration of an exogenous saccharide.

In addition, while the foregoing describes saccharide binding agents and endogenous or exogenous saccharides activators it is to be understood that the invention is not limited to such systems. Indeed, while lectin based systems will generally be limited to saccharide based activators, aptamer based systems can be designed to bind many molecules. For example, the inventive methods can be used to produce a conjugate which is activated by an endogenous or exogenous non-saccharide target molecule. In certain embodiments, such conjugates may include an affinity ligand covalently bound to the A-chain and a monovalent aptamer covalently bound to the B-chain, wherein the affinity ligand competes with the target molecule for non-covalent binding with the monovalent aptamer.

Uses

In another aspect, the present disclosure provides methods of using the conjugates. In general, the conjugates can be used to controllably activate insulin in response to an increase in glucose concentration. The invention encompasses treating diseases such as diabetes by administering a conjugate of the present disclosure to a patient in need thereof. Although the conjugates can be used to treat any patient (e.g., dogs, cats, cows, horses, sheep, pigs, mice, etc.), they are most preferably used in the treatment of humans. A conjugate can be administered to a patient by any route. In general the most appropriate route of administration will depend upon a variety of factors including the nature of the disease or condition being treated, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes including suitable pharmaceutically acceptable carriers may be found, for example, in *Remington's Pharmaceutical Sciences*, 19$^{th}$ ed., Mack Publishing Co., Easton, Pa., 1995.

Oral compositions generally include an inert diluent or an edible carrier. For the purpose of oral administration, the conjugate can be incorporated with excipients and used in the form of tablets, troches, or capsules, e.g., gelatin capsules. Oral compositions can also be prepared using a fluid carrier. Pharmaceutically compatible binding agents, and/or adjuvant materials can be included as part of the composition. For example, in certain embodiments, the tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. Compositions for oral delivery may advantageously incorporate agents to improve stability within the gastrointestinal tract and/or to enhance absorption.

In various embodiments, the conjugate may be administered by injection. The conjugate can be dissolved in a fluid carrier for ease of delivery. For example, the fluid carrier can be an aqueous solution including, but not limited to, sterile water, saline or buffered saline.

In general, a therapeutically effective amount of insulin in the form of a conjugate will be administered. By a "therapeutically effective amount" of insulin is meant a sufficient amount of the insulin to treat (e.g., to ameliorate the symptoms of, delay progression of, prevent recurrence of, delay onset of, etc.) the disease or condition at a reasonable benefit/risk ratio, which involves a balancing of the efficacy and toxicity of insulin. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the drug. Ultimate selection of an appropriate range of doses for administration to humans is determined in the course of clinical trials.

In various embodiments, the average daily dose of insulin is in the range of 10 to 200 U, e.g., 25 to 100 U (where 1 Unit of insulin is ~0.04 mg). In certain embodiments, an amount of conjugate with these insulin doses is administered on a daily basis. In certain embodiments, an amount of conjugate with 5 to 10 times these insulin doses is administered on a weekly basis. In certain embodiments, an amount of conjugate with 10 to 20 times these insulin doses is administered on a bi-weekly basis. In certain embodiments, an amount of conjugate with 20 to 40 times these insulin doses is administered on a montly basis.

It will be understood that the total daily usage of insulin (and any other drug administered in combination with a conjugate of the present disclosure) for any given patient will be decided by the attending physician within the scope of sound medical judgment. The specific therapeutically effective amount for any particular patient will depend upon a variety of factors including the disease or condition being treated; the activity of the specific insulin employed; the specific composition employed; the age, body weight, general health, sex and diet of the patient; the time of administration, route of administration and rate of excretion of the specific insulin employed; the duration of the treatment; drugs used in combination or coincidental with the specific insulin employed; and like factors well known in the medical arts. In various embodiments, a conjugate of the present disclosure may be administered on more than one occasion. For example, the present disclosure specifically encompasses methods in which a conjugate is administered by injection to a patient on a continuous schedule (e.g., once a day, once every two days, once a week, once every two weeks, once a month, etc.).

In certain embodiments, a conjugate of the present disclosure may be used to treat hyperglycemia in a patient (e.g., a mammalian patient). In certain embodiments, the patient is diabetic. However, the present methods are not limited to treating diabetic patients. For example, in certain embodiments, a conjugate may be used to treat hyperglycemia in a patient with an infection associated with impaired glycemic control. In certain embodiments, a conjugate may be used to treat diabetes.

In various embodiments, a conjugate of the present disclosure may be administered to a patient who is receiving at least one additional therapy. In various embodiments, the at least one additional therapy is intended to treat the same disease or disorder as the administered conjugate. In various embodiments, the at least one additional therapy is intended to treat a side-effect of insulin. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. For example, in certain embodiments, any of these approaches may be used to administer more than one anti-diabetic drug to a subject.

Insulin sensitizers (e.g., biguanides such as metformin, glitazones) act by increasing a patient's response to a given amount of insulin. A patient receiving an insulin sensitizer will therefore require a lower dose of an insulinconjugate of the present disclosure than an otherwise identical patient would. Thus, in certain embodiments, insulin conjugates may be administered to a patient who is also being treated with an insulin sensitizer. In various embodiments, the conjugates of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the conjugates of the present disclosure are only effective for this subclass of patients when a large number activate in a suitable timeframe. In certain embodiments, the treatment of this subclass of patients may be facilitated by combining the two approaches. Thus in certain embodiments, a traditional insulin-based therapy is used to provide a baseline level of insulin and a conjugate of the present invention is administered to provide a controlled supplement of active insulin when needed by the patient. Thus, in certain embodiments, a conjugate of the present disclosure may be administered to a patient who is also being treated with insulin. In various embodiments, the insulin may be administered at up to 75% of the normal dose required in the absence of the conjugate of the present disclosure. In various embodiments, up to 50, 40, 30 or 20% of the normal dose may be administered.

It will be appreciated that this combination approach may also be used with insulin resistant patients who are receiving an insulin sensitizer (e.g., a biguanide such as metformin, a glitazone) and/or an insulin secretagogue (e.g., a sulfonylurea, GLP-1, exendin-4, etc.).

Insulin sensitizers (i.e., drugs which potentiate the action of insulin) include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

Insulin secretagogues (i.e., drugs which stimulates insulin secretion by beta cells of the pancreas) include sulfonylureas and meglitinides. First generation sulfonylureas include tolbutamide, chlorpropamide and carbutamide. Second generation sulfonylureas which are active at lower doses include glipizide, glibenclamide, gliclazide, glibornuride and glimepiride. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may be administered in combination with amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

Kits

In another aspect the present disclosure provides kits that include conjugates (e.g., in the form of a pharmaceutical composition which includes the conjugate with a pharmaceutically acceptable carrier). In various embodiments, the composition is designed for injection and the kit includes a syringe or pen. In various embodiments, a kit may include a syringe or pen which is pre-filled with a pharmaceutical composition that includes the conjugate with a liquid carrier. Alternatively, a kit may include a separate container (e.g., a vial) with a pharmaceutical composition that includes the conjugate with a dry varrier and an empty syringe or pen. In certain embodiments, such a kit may include a separate container (e.g., another vial) with a liquid carrier that can be used to reconstitute a liquid pharmaceutical composition that can then be taken up into the syringe or pen. In certain embodiments, a kit may include written instructions for preparing and administering a cojugate or pharmaceutical composition of the present disclosure.

EXAMPLES

Example 1

Synthesis of Azidoethylglucose (AzEG)

a. Synthesis of bromoethylglucose

DOWEX 50Wx4 resin (Alfa Aesar, Ward Hill, Mass.) was washed with deionized water to remove color. A mixture of 225 gm D-glucose (1.25 mol; 1 equiv., Alfa Aesar) and 140 gm DOWEX 50Wx4 was treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction was monitored by TLC (20% methanol/ dichloromethane (DCM)). Reaction was complete after about four hours, and it was allowed to cool to room temperature. The solution was filtered to remove the resin, and the resin washed with ethyl acetate and DCM. The resulting filtrate was stripped to an amber oil in a rotory evaporator to give a total of 400 g after stripping.

The amber oil was purified on silica gel (4 kg silica packed in DCM) in the following manner. The crude was dissolved in DCM and loaded onto the column, and then eluted with 2×4L 10% methanol/DCM; 2×4L 15% methanol/DCM; and 3×4L 20% methanol/DCM. Product containing fractions (on the basis of TLC) were pooled and stripped to dryness to afford 152 gm of 1-α-bromoethyl-glucose (42%).

b. Conversion of Bromoethylglucose to Azidoethylglucose (AzEM)

A 5L round bottom three-necked flask, equipped with a heating mantle, an overhead stirrer, and a thermometer, was charged with 150 gm bromoethylglucose (525 mmol). The oil was dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution was cooled to room temperature and concentrated to dryness on the rotovap. The solid residue was digested with 3×500 mL of 5:1 vol. $CHCl_3$:MeOH at 40 C. The combined organic portions were filtered and evaporated to dryness to afford azidoethylglucose (86 gm) as an off-white solid. TLC (20% MeOH/DCM; char with $H_2SO_4$): single spot, indistinguishable from the starting material.

c. Repurification of Azidoethylglucose 32 gm of azidoethylglucose was taken into 100 mL water. The turbid solution was filtered through a glass microfibre filter (Whatman GF/B). The golden filtrate was evaporated to a solid on a rotovapor. The solid was taken into methanol (100 mL) and the turbid solution was again filtered through a glass microfibre filter. The resulting pale yellow filtrate was stripped to a solid under vacuum.

The solid was taken into a minimum of methanol (50 mL) and ethyl acetate (150 mL) was added slowly with stirring. The heavy slurry was cooled and filtered. The solid was air dried (hygroscopic) and put in a 60 C oven overnight. TLC has very little origin material. Yield 15.4 gm. The Mother Liquor was evaporated under vacuum to a yellow gum. No attempt was made to further purify this material at this time.

Example 2

Synthesis of Azidoethylmannose (AzEM)

a. Synthesis of Bromoethylmannose

DOWEX 50Wx4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50Wx4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/ dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotory evaporator.

The amber oil is purified on silica gel (4 kg silica packed in DCM) in the following manner. The crude is dissolved in DCM and loaded onto the column, and then eluted with 2×4L 10% methanol/DCM; 2×4L 15% methanol/DCM; and 3×4L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. $CHCl_3$:MeOH at 40 C. The combined organic portions are filtered and evaporated to dryness to afford azidoethylmannose as an off-white solid.

c. Repurification of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 3

Synthesis of Azidoethylmannobiose (AzEBM)

The AzEM compound from Example 2 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 4

Synthesis of Azidoethylmannotriose (AzETM)

a. 1-α-bromo-2,3,4,6-tetrabenzoyl-mannose

To a 500 mL 3-neck flask containing a stir bar and nitrogen inlet was added 40 gm (60.9 mmol) of pentabenzoylmannose and 80 mL methylene chloride. The resulting solution was cooled in an ice bath to <5 C, and 80 mL 33% HBr-acetic acid solution was added via an addition funnel at such a rate to maintain the reaction temperature <10 C. Upon complete addition (~30 min.) the ice bath was removed and stirring was continued for 3 hours.

The reaction solution was diluted with an equal volume (160 mL) of DCM and extracted successively with water (2×500 mL), saturated bicarbonate (2×50 mL) and Brine (1×50 mL), dried over magnesium sulfate and the solvent evaporated to give 41 gm of solid foam. (Theoretical yield 40.1 gm) and was stored under $N_2$ in a freezer. This material was used without further purification. The reaction was monitored by TLC: silica gel (Hexane/Ethyl Acetate, 7/3) starting material $R_f$ 0.65, product $R_f$ 0.8 UV visualization. $^1$H NMR (CDCl$_3$) δ 8.11 (d, 2H), 8.01 (m, 4H), 7.84 (d, 2H), 7.58 (m, 4H), 7.41 (m, 6H) 7.28 (t, 2H), 6.58 (s, 1H), 6.28 (m, 2H), 5.8 (m, 1H), 4.75 (dd, 1H) 4.68 (dd, 1H) 4.5 (dd, 1H).

b. 1-Azidoethyl-2,4-dibenzoylmannose

To a 1.0L, 3-neck flask containing a stir bar, nitrogen inlet and 300 mL of anhydrous acetonitrile was added 25 gm 1-azidoethylmannose (100.4 mmole), and 50 mL triethyl orthobenzoate (220 mmole, 2.2 equiv.). The resulting slurry was stirred at room temperature and 0.8 mL (10 mmole) trifluoroacetic acid (TFA) was added neat. The solution cleared within 10 minutes and stirring was continued for an additional two hours, then 25 mL of 10% aqueous TFA was added and stirring was continued for an additional 2 hours to hydrolyze the intermediate to the ester isomers. The solvent was evaporated under vacuum to a viscous oil, which was triturated with 50 mL DCM and again evaporated to a viscous oil.

Toluene (70 mL) was added to the residue and the viscous solution was seeded with 2,4-dibenzoylazidoethylmannose. A fine precipitate formed within 15 minutes and stirring was continued overnight at room temperature. The resulting heavy suspension was set in the freezer for 2-4 hours, then filtered and the solid washed with ice cold toluene (2×10 mL). The solid was air dried to a constant weight to give 21 gm (TY 22.85 gm @ 50% isomeric purity) of ~95% isomeric purity. The product was taken into 40 mL toluene, stirred for 1 hour and then set in the freezer for an additional 2 hours. The solid was filtered and washed (2×10 mL) with ice cold toluene and air dried to a constant weight to give 18.5 gm of the single isomer product 2,4-dibenzoylazidoethylmannose in 83% yield. The mother liquors contained the undesired isomer and a small amount of the desired isomer. The reaction was monitored by TLC: SG (Hexane/Ethyl Acetate 7/3) Starting Material $R_f$ 0.0, orthoester intermediate $R_f$ 0.9. (Hexane/Ethyl Acetate: 8/2) SM $R_f$ 0.8, desired isomer $R_f$ 0.4, un-desired isomer $R_f$ 0.2

$^1$H NMR 300 MHz (CDCl$_3$) δ 8.12 (t, 4H), 7.66 (t, 2H), 7.5 (m, 4H), 5.56 (t, 1H), 5.48 (m, 1H), 5.14 (m, 1H), 4.5 (dd, 1H), 4.0 (m, 2H), 3.8 (m, 3H), 3.56 (m, 1H), 3.44 (m, 1H).

c. Perbenzoylated-man(α-1,3)-man(α-1.6)-α-1-azidoethylinannopyranoside

To a 1.0 L 3-neck flask with a stir bar, nitrogen inlet was added 41 gm crude 1-bromo-tetrabenzoymannose (60.9 mmole, ~2.5 equiv.) in 185 mL DCM. To this was added 11.2 gm 2,4-dibenzoylazidoethylmannose (24.5 mmole) followed by 11.2 gm 4A sieves. The slurry was stirred a room temperature for 10 minutes and cooled to ~15° C. in a methanol/ice bath.

In a separate dark vessel was added 190 mL toluene followed by 15.1 gm silver-trifluoromethanesulfonate (AgOTf) (58.8 mmole, 2.4 equiv.) and was stirred into solution in the dark. This solution was transferred to a large addition funnel, and added drop-wise to the stirring suspension, while protecting the reaction from light. The reaction temperature was maintained <–10 C by adjusting the AgOTf addition rate. Upon complete addition (–30 minutes) the cold bath was removed and the reaction stirred for an additional 2 hours until a single product remained by TLC (SG, Hexane/Ethyl Acetate: 7/3, Bromo $R_f$ 0.9, azido $R_f$ 0.4, trios product $R_f$ 0.5, uv visualization).

Triethylamine (7 mL, 5.0 equiv.) was added followed by 200 mL DCM. The resulting slurry was filtered through a pad of silica gel and celite and washed with 2×75 mL DCM. The solvent was evaporated under vacuum and the residue taken into ethyl acetate and washed sequentially with water (2×100 mL), bicarb (2×50 mL), brine (1×75 mL) and dried over magnesium sulfate. The solvent was evaporated under vacuum to give 39 gm of solid foam (TY 39.5 gm). $^1$H NMR 300 MHz (CDCl$_3$) δ 8.3 (d, 2H), 8.2 (m, 8H), 7.85 (d, 4H), 7.75 (dd, 4H), 7.3-7.65 (m, 30H), 7.2 (t, 2H), 6.05 (m, 4H), 5.9 (t, 2H), 5.63 (m, 2H), 5.38 (s, 2H), 5.18 (d, 1H), 4.65 (m, 4H), 4.5 (m, 2H), 4.35 (m, 4H), 3.8 (m, 2H), 3.54 (m 2H).

d. Man(α-1,3)-man(α-1.6)-α-1-azidoethylmannopyranoside

To a stirring suspension of 3.0 gm perbenzoylated-man (α-1,3)-man(α-1.6)-α-1-azidoethylmannopyranoside (1.86 mmole) in 40 mL methanol was added 0.2 mL 4.28M sodium methoxide in methanol. The resulting suspension was stirred 20 hours at room temperature giving a clear solution. The completion of the reaction was monitored by TLC, (SG, hexane/ethyl acetate: 8/2 SM $R_f$ 0.4, product $R_f$ 0.0).

The methanol was evaporated under vacuum giving an oily semi-solid. The residue was taken into ethyl acetate (50 mL) and stirred for 3 hours. The solid was filtered, washed with fresh ethyl acetate (2×20 mL) and air dried to a constant weight to give 1.09 gm (TY 1.07 gm) of product. The mother liquors contained residual methyl benzoate, the de-protection by-product.

Example 5

Synthesis of Aminoethyl-Sugars (AEG, AEM, AEBM, AETM) from Azidoethyl-Sugars (AzEG, AzEM, AzEBM, AzETM)

The azido-terminated compounds from Examples 1-4 are readily hydrogenated at room temperature by using palladium/carbon catalyst, a small amount of acetic acid, and ethanol as a solvent to give the corresponding amine-terminated compounds. FIG. 2 shows the chemical structures of AEG, AEM, AEBM, AETM. The process is identical to the one described for AETM below, except that those skilled in the art will understand that the amounts of reagents, solvents, etc. should be scaled to the number of moles of sugar-ligand to be hydrogenated.

a. Man(α-1,3)-Man(α-1.6)-α-1-aminoethylmannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC (SG, Methanol, SM $R_f$ 0.75, Pdt $R_f$ 0.0, PMA vis.). The suspension was filtered over celite, which was rinsed with ethanol (2×50 mL) and the filtrate concentrated under vacuum.

HPLC of this material (C18, 3% Acetonitrile/97% 0.1% $H_3PO_4$, 220 nm, 2 ml/min) gave uv adsorption of the injection column void material, Rt 2.5 minutes, indicative of benzoate ester.

The filtrate was diluted with 70 mL water and 12 mL of 1N NaOH and the solution stirred overnight at room temperature (HPLC: no uv material at column void Rt 2.5 min., uv material at Rt 10.5 minutes co-eluting with benzoic acid). 2 gm of decolorizing charcoal were added and the stirring suspension heated to 80 C, cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid by-products. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for 5 hours to give 4.1 gm of a white granular solid (TY 5.1 gm). The NMR was clean of any aromatic protons. $^1$H NMR 300 MHz ($D_2O$) δ 5.08 (s, 1H), 4.87 (s, 1H), 4.81 (s, 1H), 4.8-3.6 (m, 18H), 2.9 (m, 2H).

Example 6

Dipropargyl Sugar Synthesis and Production of AE-Ligand a. Synthesis of diethyl dipropargylmalonate Diethylmalonate (122.5 g, 0.7648 mol) was added to absolute ethanol (800 ml) containing sodium ethoxide (prepared from sodium metal, 38.5 g, 1.67 mol). After 30 min, propargyl bromide (200 g, 1.68 mol) was slowly added to the stirred suspension, keeping the temperature under 60 C. The mixture was refluxed overnight (15 hours). The precipitated salts were removed by filtration and washed with ethanol. Solvent was removed in vacuo, and the residue diluted with water and extracted with ethanol (2×200 ml). The combined extracts were dried over MgSO4, filtered, washed with Et2O and the solvent removed in vacuo to afford a golden colored oil. The oil was placed on high vacuum (40 C) for 3 hours and allowed to stand. Solids began to crystallize forming an oily solid. Let stand overnight (16 hours). Cyclohexane was charged to flask, solids broken-up, filtered, and washed with cyclohexane to afford white crystalline product (81 gm, 44.8% yield). Reaction was followed by GC.

b. Synthesis of dipropargylmalonic Acid

Diethyl dipropargyl malonate (80 gm, 0.339 mol) was refluxed in 600 ml of 10% alcoholic potassium hydroxide overnight (15 hours). Solvent was removed in vacuo and the residue was acidified with 3N HCl. The residue was extracted with Et2O (2×300 ml). The combined extracts were dried over MgSO4, filtered, washed with Et2O and concentrated in vacuo to an oil. Placed on high vac (40 C) for 2 hours and let stand to afford dipropargylmalonic acid as an oil (46 gm, 75.4% yield). Reaction was followed by GC.

c. Synthesis of Dipropargylacetic Acid

The dipropargylmalonic acid (26 gm, 0.443 mol) was heated neat at 135 C until $CO_2$ stopped evolving. It was then allowed to cool to an oil. The oil was distilled at 0.5 psi. The remaining oily residue in the distillation flask and solid were combined (15.7 gm, 79.9% yield) and was used as is in the next step.

d. Synthesis of [2-(3-prop-2-ynyl-hex-5-ynoylamino)-ethyl]-carbamic acid t-butyl ester N-boc-ethylenediamine (18.3 gm, 0.1143 mol) in 50 ml of $CH_3CN$ was added slowly via an addition funnel to a stirred solution containing dipropargylacetic acid (15.56 gm, 0.1143 mol), TBTU (36.74 gm, 0.114 mol) and DIPEA (29.6 gm, 0.229 mol) in 300 ml of $CH_3CN$ at 0 C. Precipitation occurred. The ice bath was removed and the product was stirred at ambient temperature overnight (16 hours). The reaction was now totally homogeneous. The solution was concentrated in vacuo and the residue was diluted with 800 ml of water. The resulting solids were filtered, washed copiously with water, and vacuum dried to give 14.3 gm of crude product. Re-crystallization (2×) from DCM, filtration and washing with hexanes affords the product (9.85 gm, 31% yield, 98% purity by HPLC (214 nm)).

e. Click Reaction of Azidosugar to [2-(3-prop-2-ynyl-hex-5-ynoylamino)-ethyl]-carbamic acid t-butyl ester To 1.1 dipropargyl-acetyl-(-1N,2N—BOC-1,2-diaminoethyl)amide (DP, 418 mg, 1.5 mmole) in DCM (20 mL) was added drop-wise TFA (4 mL) over 5 minutes at 0 C. The darkening solution was stirred at room temperature overnight. The volatiles were evaporated under reduced pressure. Toluene (20 mL) was added to the residue and stripped under reduced pressure two times. The resulting dark oil was used without further purification.

To this residue was added THF (20 mL) and water (20 mL) with stirring for 15 minutes. Copper Sulfate (225 mg, 0.9 mmole) was added followed by sodium ascorbate (180 mg, 0.9 mmole). The resulting mixture was heated to 55-60 C for 6 hours and then stirred at room temperature for 18 hours. The solution was evaporated under reduced pressure to approx. half volume and filtered through a microfibre glass filter. The resulting clear solution was placed on a resin column (Dowex 50X-2) which was washed with water (6×75 mL) until neutral pH, and then washed with 10% $NH_4OH$ (8×75 mL). The fractions staining positive with Ninhydrin were combined and evaporated under reduced pressure to a glassy solid. The glass residue was taken into water (250 mL) and treated with 0.5 gm charcoal and heated to reflux. The cooled slurry was filtered over celite and a microfibre filter. The resulting pale yellow solution was evaporated to a glassy solid under reduced pressure and methanol was added and evaporated (2×) to give a off white foam (0.9 gm, TY 1.0 gm).

Example 7

Tripropargyl Sugar Synthesis and Production of AE-Ligand a. 2-(2-BOC-aminoethyl)thioacetamide-tris[(propargyloxy)methyl]aminomethane To a solution of t-butyl N-(2-mercaptoethyl)carbamate (Frontrun Organix, Ipswich, Mass.; 177.26 mg, 1 mmole) in ethanol (5 mL) was added NaOH (1.1 mmole) with stirring at room temperature. To this solution was added 2-bromoacetamide-tris[(propargyloxy)methyl]aminomethane (356 mg, 1.0 mmole, see J. Org. Chem. 73, 5602, 2008) and stirring was continued for 20 hours (TLC SG 8/2 hexane/ethyl acetate, pdt $R_f$ 0.4). The solvent was evaporated under vacuum and the residue was taken into ethyl acetate (40 mL) and washed successively with water (25 mL), 0.5 N NaOH (25 mL) and Brine (25 mL), dried over $Na_2SO_4$ filtered and concentrated to an oil (360 mg, TY 452.3 mg). NMR $CDCl_3$, (ppm): 7.05 (s, 1H, N—H); 5.25 ((s, 1H, N—H); 4.85 (s, 6H); 3.85 (s, 6H); 3.3 (m, 2H); 3.15 (s, 2H); 2.7 (m, 2H); 2.42 (s, 3H); 1.22 (s, 9H).

b. 2-(2-aminoethyl)thioacetamide-tris[(triazolo-1-(2-ethylmannose) 4-methoxy)methyl]aminomethane To a stirring solution of 2-(2-BOC-aminoethyl)thioacetamide-tris[(propargyloxy)methyl]aminomethane (1 gm, 2.21 mmole) in DCM (40 mL) at room temperature was added TFA (4 mL) dropwise. The resulting solution was stirred overnight. The solvents were removed under vacuum and the residue taken into toluene (15 mL) and evaporated to dryness.

The residue was taken into THF (40 mL), water (40 mL) and stirred into solution. Azidoethylmannose (3.75 eq., 2.0 gm, 8.3 mmole) was added followed by copper sulfate (500 mg, 2.0 mmole) and sodium ascorbate (400 mg, 2.0 mmole) and the resultant mixture stirred at 55-60 C (oil bath) for 6 hours, cooled to room temperature and stirred overnight. The resulting mixture was concentrated under vacuum to one half volume and filtered thru a micro-glass filter. The filtrate was loaded on a resin column (Dowex 50w 50×4-100) and eluted with water (6×75 mL) until neutral. The column was then eluted with 15% Ammonium Hydroxide (10×75 mL) and the fractions positive to ninhydrin were pooled and concentrated to a glassy foam (1.29 gm, TY (MW 1099 g/mol), 53% over two steps).

Example 8

Preparation of $NH_2$-A1-di-MSC-(B1, B29)-insulin 300 mg of zinc free recombinant human insulin (Sigma-Aldrich, St. Louis, Mo.) is dissolved in 15 ml of 80% pyridine. 0.35 ml of Boc azide is added and the mixture is incubated at 30 C overnight. The crude product is precipitated by adding 10 volumes of cold acetone, collected by centrifugation, and purified by SP-Sephadex C25 ion-exchange chromatography, using a solution of water/isopropanol/acetic acid (51:40:9 by volume, pH adjusted to 3.0 by ammonium hydroxide) with a NaCl gradient (0.05-0.25 M) elution. The main peak N-A1-Boc-insulin is collected.

The next step is the blocking of B1 and B29 amino groups by Msc groups. 93 mg of N-A1-Boc-insulin are dissolved in 4 ml of dimethyl sulfoxide (DMSO). The pH is adjusted to 8.0 by N-methylmorpholine. Next, 13 mg of Msc N-succinimidyl ester (Msc-ONSu) dissolved in 2 ml of DMSO are added and the reaction mixture is incubated at 25 C. After 1 hour, the reaction is stopped by adding 2.7 ml of glacial acetic acid. The reaction mixture is then superdiluted by 10× in pH 8.2 HEPES buffered saline followed by size exclusion chromatography on a Biogel P2 column (Econopak, Bio-rad labs) in DI water and subsequent lyophilization. This material is then dissolved at 25 mg/ml and further purified to obtain the desired product using preparative reverse phase HPLC on a Waters SymmetryPrep C18, 7 um, 19×150 mm column. Buffer A is deionized water containing 0.1% TFA and Buffer B is acetonitrile containing 0.1% TFA. Before purification, the column is equilibrated at 15 ml/min with a 80% A/20% B mobile phase using a Waters DeltaPrep 600 sytem. Approximately 5 ml of the crude solution is injected onto the column over the course of 2 minutes at a flow rate of 15 ml/min after which a linear gradient is employed from 80% A/20% B to 75% A/25% B over the next 5 minutes followed by a slower linear gradient from 75% A/25% B to 62% A/38% B over the next 22 minutes. Once collected, the solution is rotovapped to remove acetonitrile and lyophilized to obtain the pure BOC-A1-di-MSC-(B1, B29)-insulin conjugate.

Finally, the A1-BOC protecting group is removed by dissolving the lyophilized powder in 90% TFA/10% anisole for one hour at 4° C. followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then lyophilized to obtain the pure $NH_2$-A1-di-MSC-(B1, B29)-insulin conjugate

Example 9

DSS Conjugation of $NH_2$-A1-di-MSC-(B1,B29)-Insulin with Aminoethylsugar Affinity Ligands Disuccinimidyl suberate (DSS) obtained from Molecular Biosciences (Boulder, Colo.) containing N=2 activated ester groups is dissolved at 60 mM in 1.0 ml of anhydrous DMSO followed by the addition of 400 ul (excess) of triethylamine (TEA). The solution is stirred rapidly for 10 minutes at room temperature. The $NH_2$-A1-di-MSC-(B1,B29)-insulin is then dissolved separately in 7.9 ml of DMSO at a concentration of 7.4 mM. Once dissolved, the entire $NH_2$-A1-di-MSC-(B1, B29)-insulin solution is added dropwise over the course of 10 min to the DSS/DMSO/TEA solution followed by room temperature mixing for two hours. The remaining activated ester is then reacted with the amine-functionalized sugars (AEG, AEM, AEBM, or AETM) in the following manner. A 480 mM solution of affinity ligand is prepared in an appropriate volume of dry DMSO. Once dissolved, enough solution is added to provide a number of reactive equivalents equal to three times the number of moles of DSS in the reaction mixture. After the affinity ligand solution is added, the solution is stirred for one more hour at room temperature to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified using Econo-pak columns packed with Biogel P2 (Bio-rad Laboratories). The solution passing through the column void volume is then concentrated using Amicon 3K centrifugal filters (Millipore, Billerica, Mass.) to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/min with a 80% A/20% B mobile phase using a Waters DeltraPrep 600 sytem. Approximately 5 ml of the crude solution is injected onto the column over the course of 2 minutes at a flow rate of 15 ml/min after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the affinity ligand. Once collected, the solution is rotovapped to remove acetonitrile and lyophilized to obtain a pure conjugate whose identity may be verified by LC-MS (HT Laboratories, San Diego, Calif.).

Finally, the MSC protecting groups are removed by dissolving the lyophilized powder in 2N NaOH at 0 C for 5 minutes followed by rapid neutralization with glacial acetic acid to pH 7 and 10× superdilution in HEPES pH 8.2 buffer containing 0.150M NaCl. The resulting solution is passed through a Biogel P2 column to remove impurities and eluted into DI water. The deprotected, purified aqueous conjugate solution is then lyophilized until needed.

| Synthesis Conditions | | Expected Product Characterization | |
|---|---|---|---|
| Affinity Ligand | AE-sugar MW | MW (LC-MS) | Sugar/Insulin |
| AEG | 223 | 6157 | 1.0 AEM |
| AEM | 223 | 6157 | 1.0 AEBM |
| AEBM | 385 | 6319 | 1.0 AETM |
| AETM | 547 | 6481 | 1.0 AEM |

Example 10

B29-BOC-Protection of the A-Chain-Affinity Ligand-Modified Insulin (AAMI)

0.7 mmol of the A-chain-affinity ligand-modified insulin (AAMI) synthesized according to Example 9 is dissolved in 100 ml of anhydrous DMSO at room temperature followed by the addition of 4 ml of triethylamine (TEA). The solution is stirred for 30 min at room temperature. Next, 0.9 ml (1.3 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 ul aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 μl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder.

A preparative reverse phase HPLC method is used to isolate the pure B29-BOC-AAMI from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/min with a 70% A/30% B mobile phase using a Waters DeltraPrep 600 system. Approximately 5 ml of the crude powder solution is injected onto the column at a flow rate of 15 ml/min over the course of 5 minutes after which a linear gradient is employed from 70% A/30% B to 62% A/38% B over the course of the next 3.5 minutes and held there for an additional 2.5 minutes. Once the desired peak is collected, the solution is rotovapped to remove acetonitrile and lyophilized to obtain the pure $NH_2$-B1-B29-BOC-AAMI. Identity is verified by LC-MS (HT Laboratories, San Diego, Calif.) and site of conjugation determined by N-terminal sequencing (Western Analytical, St. Louis, Mo.).

Example 11

Coupling of ABDA to B29-BOC-Protected AAMI and Subsequent Deprotection

Aminobutyraldehyde diethyl acetal (ABDA, Sigma Aldrich, St. Louis, Mo.) and the B29-BOC-protected AAMI may be reacted to a DSS framework through the terminal activated esters to produce AAMI-B1-DSS-ABDA. Approximately one equivalent of the AAMI as a 40-50 mg/ml solution in DMSO is added at room temperature to a 50 mg/ml solution of DSS in DMSO containing excess triethylamine and allowed to react for approximately one hour. Next, an excess of ABDA (2-10 equivalents) as a 100 mg/ml solution in DMSO is added and allowed to react for an additional 2 hours.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified using Econo-pak columns packed with Biogel P2 (Bio-rad Laboratories). The solution passing through the column void volume is then concentrated using Amicon 3K centrifugal filters (Millipore, Billerica, Mass.) to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/min with a 80% A/20% B mobile phase using a Waters DeltraPrep 600 sytem. Approximately 5 ml of the crude solution is injected onto the column over the course of 2 minutes at a flow rate of 15 ml/min after which a linear gradient is employed from 80% A/20% B to 75% A/25% B over the next 5 minutes followed by a slower linear gradient from 75% A/25% B to 62% A/38% B over the next 22 minutes. Once the desired peak is collected, the solution is rotovapped to remove acetonitrile and lyophilized to obtain a pure conjugate whose identity may be verified by LC-MS (HT Laboratories, San Diego, Calif.).

Finally, the diethyl acetal and BOC protecting groups are removed by dissolving the lyophilized powder in a 90% TFA/10% anisole solution for one hour at 4 C followed by 10× superdilution in HEPES pH 8.2 buffer containing 0.150M NaCl and subsequent pH adjustment to 6.5. The resulting solution is passed through a Biogel P2 column to remove impurities and eluted into pH 6.5 HEPES buffered saline. Finally, the resulting aqueous conjugate solution may be concentrated to the desired level using Amicon 3K centrifugal membrane filters.

The resulting conjugate now contains an A1-substituted affinity ligand and a B1-reactive aldehyde group which may then be reacted with any amine-containing glucose binding molecule.

Example 12

Monomeric Con A

A monovalent monomer derivative of ConA (Mm-Con A) can be prepared as described previously (Saito et al., *J. Biol. Chem.* 256: 7499-7505, 1983 and Tanaka et al., *J. Biochem. (Tokyo)* 89:1643-1646, 1981) by photoalkylation of ConA using chloroacetamide. This monomer preparation, which is purified to the final purification stage by affinity chromatography and gel filtration, can be demonstrated to be completely free of both dimers and tetramers by the analytical rechromatography on Sephadex G-100 and by gel filtration through a column of Bio-Gel P-100. The Mm-ConA preparation can also be shown to be completely monomeric by the velocity and equilibrium sedimentation experiments.

Example 13

PEGylated Monomeric Con A

The monomeric Con A of Example 12 may be pegylated. PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs. In preferred embodiments PEGs are covalently attached to an amino group, especially the free amino group found in lysine residues.

Numerous methods for directly attaching PEGs to proteins are described in Delgado et al., *Crit. Rev. Thera. Drug Carrier Sys.* 9:249-304, 1992; Francis et al., *Intern. J. of Hematol.* 68:1-18, 1998; U.S. Pat. Nos. 4,002,531; 5,349,052; WO 95/06058; and WO 98/32466. One such method uses tresylated monomethoxy poly(ethylene glycol) (MPEG), which is produced by reacting MPEG with tresylchloride ($ClSO_2CH_2CF_3$). Tresylated MPEG reacts with exposed amine groups on lectins. A skilled person will recognize that the invention is not limited to any specific pegylation agent and will be able to identify other suitable compounds that are known in the art. In certain embodiments PEGs may be attached via an intervening linker. For example, U.S. Pat. No. 5,612,460, discloses urethane linkers for connecting PEG to proteins. PEGs can be attached to a protein via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional PEG derivatives and reaction chemistries for attaching PEG to proteins are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogues can be obtained from these commercial PEG suppliers that describe a range of suitable PEG compounds and chemistries (e.g., see the Nektar Advanced PEGylation CATALOG 2004).

The following specific example describes the preparation of a pegylated composition using "PEG-10-5k" molecules (where 10 refers to the number of moles of PEG reagent added to the reaction mixture per mole of monomeric Con A and 5k refers to the molecular weight of the PEG reagent in Da). Other pegylated Con A compositions can be prepared using slight variations on this general method (e.g., different pegylation reagent, different ratios of reagents, different pH and/or temperature, different buffers, etc.). See in particular the methods described in US 2007/0110811.

100 mg of the monomeric Con A of Example 12 is dissolved in 10 ml of 100 mM BES buffer at pH 7.4 containing 1 M NaCl, 1 mM $CaCl_2$ and 1 mM $MnCl_2$. The resulting mixture is stirred at room temperature until all components are dissolved. Separately, 190 mg of the pegylation agent mPEG-SPA-5K (succinimidyl propionic acid activated mPEG, MW 5 kD, Nektar Therapeutics, San Carlos, Calif.) is added to 1.90 ml of 100 mM BES buffer at pH 7.4 containing 1 M NaCl, 1 mM $CaCl_2$ and 1 mM $MnCl_2$ and vortexed until dissolved. This mixture is then slowly added dropwise using a pipette to the above solution at room temperature. The amount of pegylation agent is adjusted so that the molar ratio of pegylation agent to Con A monomer is about 10. After addition, the resulting solution is stirred overnight at room temperature. The following day the solution is ultrafiltered at room temperature using a 200 ml size stirred cell (Amicon Model 3000, Millipore Corporation, Billerica, Mass.) using a 50 kD MW cut-off filtration disc (Millipore Corporation, Billerica, Mass.). The solutions are extensively ultrafiltered against 100 mM BES buffer at pH 7 containing 1000 mM NaCl, 1 mM $CaCl_2$ and 1 mM $MnCl_2$ to remove unreacted pegylation agent, and then extensively against deionized water containing 1 mM $CaCl_2$ and $MnCl_2$. The role of manganese and calcium ions has been described previously (Sophianopoulos et al., *Prep. Biochem.* 11:413-435, 1981). The resulting solution is then lyophilized to yield the PEGylated Con A monomer.

In general, the number of PEG molecules that are attached to each Con A monomer (i.e., the degree of substitution) will vary based on the nature of the PEG molecule and the reaction conditions. Each Con A monomer includes twelve lysine residues. As a result, if monomeric Con A is pegylated with a PEG molecule that reacts with lysine residues, then each monomer could be covalently linked to 1, 2, 3, 4, 5, 6, 7, 8, 9, 10, 11 or 12 of these PEG molecule. Methods for determining the degree of substitution are discussed in Delgado et al., *Crit. Rev. Thera. Drug Carrier Sys.* 9:249-304, 1992. In various embodiments, the pegylated composition will include a mixture of Con A monomer species with different degrees of substitution. In certain embodiments, a pegylated composition may be further processed in order to enrich one or more of these monomeric species. In general, any method that is capable of differentiating monomers with different degrees of substitution (e.g., ion exchange chromatography, affinity chromatography, size exclusion chromatography, etc.) may be used for this purpose. Suitable methods are described in US 2007/0110811. In certain embodiments, these methods may produce compositions with highly pegylated monomers (e.g., with 6-11, 7-11, 8-11, 9-11, 10-11 or 11 substitutions).

In general, one of the lysines is preferably left unreacted so that it can be used for conjugation to insulin as discussed in Example 14.

Example 14

Coupling of A1-Affinity Ligand-B1-Aldehyde-Insulin to Monovalent Glucose Binding Molecule A 5 mg/ml solution of A1-affinity ligand-B1-aldehyde-insulin synthesized according to Example 11 is mixed with a 5× molar excess of glucose-binding molecule (e.g., the Mm-Con A from Example 12 or a PEG-Mm-Con A from Example 13) dissolved in a pH 6.5 buffered saline solution. Separately, a stock solution of reducing agent is prepared by dissolving 1.5 g of sodium cyanoborohydride (Sigma Aldrich, St. Louis, Mo.) in 15 ml of a 20 mM HEPES pH 7.0 buffer containing 0.150 M NaCl and the pH carefully adjusted to 6.5 with dilute HCl solution. Enough cyanoborohydride stock solution is added to the conjugate-glucose binding molecule solution to achieve a final concentration of 12.5 mg/ml. The resulting solution is then allowed to react overnight at room temperature. The resulting aqueous solution is then purified by size exclusion using an appropriate solid phase for the desired separation of conjugated and unconjugated glucose-binding molecules. Once collected, the solution can be dialyzed against DI water and lyophilized until further needed.

Example 15

Glucose-Clamps to Determine Glucose-Dependent Conjugate Bioactivity

To test the bioactivity of the resulting conjugates as a function of glucose concentration, the following glucose clamp method is used. Double jugular vein (JV/JV) catheterized rats are maintained at a desired target glucose value (100, 200, 300 or 400 mg/dl) for extended periods of time by infusing a 50% dextrose solution through the catheter line. In this type of experiment two key parameters are followed: (a) the target blood glucose level which is set by design and maintained at a particular level by adjusting (b) the glucose infusion rate (GIR). After the conjugate is injected subcutaneously at given dose (U/kg), the GIR is adjusted to compensate for the glucose-lowering activity of the conjugate. Blood glucose levels are sampled frequently via tail vein bleeding and the glucose infusion rate (GIR) varied to compensate for any drift. The GIR required to maintain the glucose levels at a given target concentration therefore measures the bioactivity of the conjugate at that given glucose concentration. The higher the GIR, the higher the conjugate bioactivity. The same experiments are performed on rats receiving just a saline injection to determine the background GIR levels for each desired target glucose level. The increase in GIR following injection of the conjugate over these baseline levels can then be plotted as a function of target glucose concentration. The same experiments are also performed using unmodified insulin and the increase in GIR following injection of the unmodified insulin over the baseline levels can then be plotted as a function of target glucose concentration. Inventive conjugates will have substantially reduced GIR requirements at a target glucose concentration of 100 mg/dl compared to unmodified insulin and substantially the same or greater GIR requirements at target glucose concentrations of 200, 300, and/or 400 mg/dl as compared to unmodified insulin.

Example 16

Monomeric Glucose-Binding Polynucleotide Aptamers

This example describes the preparation of exemplary monomeric glucose-binding polynucleotide aptamers. In certain embodiments these could be used instead of the monomeric Con A of Examples 12 and 13. Nuclease-resistant RNA sequences were identified that bind to immobilized glycogen at glucose concentrations <50 mg/dL and elute over a wide range of increasing glucose concentrations. An initial library of $10^{15}$-$10^{16}$ sequences was constructed according to established methods, for a DNA oligonucleotide with a sequence comprised of a T7 promoter region followed by a 20 base pair (bp) 5' primer, a 40 bp random region, and a 20 bp 3' primer site. T7 RNA polymerase was used with 2'-fluoro-2'-deoxy-pyrimidine 5'-triphosphates (2'-F-CTP and 2'F-UTP) in order to transcribe the modified RNA aptamers, which were used in a SELEX process with a cyanogen-bromide crosslinked oyster glycogen (MW=500,000 g/mol, Sigma Aldrich) as the binding stationary phase.

After six rounds of selection one viable monoclonal sequence (30106K1) was found that had any glycogen bead binding affinity. 30106K1 was reverse-transcribed and mutated according to an existing methodology (see below), and the new pool was reselected using glycogen bead binding and glucose elution selection methodology in an attempt to obtain a sequence homologous family of aptamers in order to discover the minimal sequence motif necessary for reversible binding to the glycogen stationary phase.

After mutagenesis, two more rounds of selection were performed, and the resulting mixture was tested to obtain monoclonals, which were then sequenced to obtained 28 monoclonals, 7 of which were unique. Several of the sequences had a great deal of homology, while sequences 1, 4 and 6 differed substantially from the others.

Figure 4:
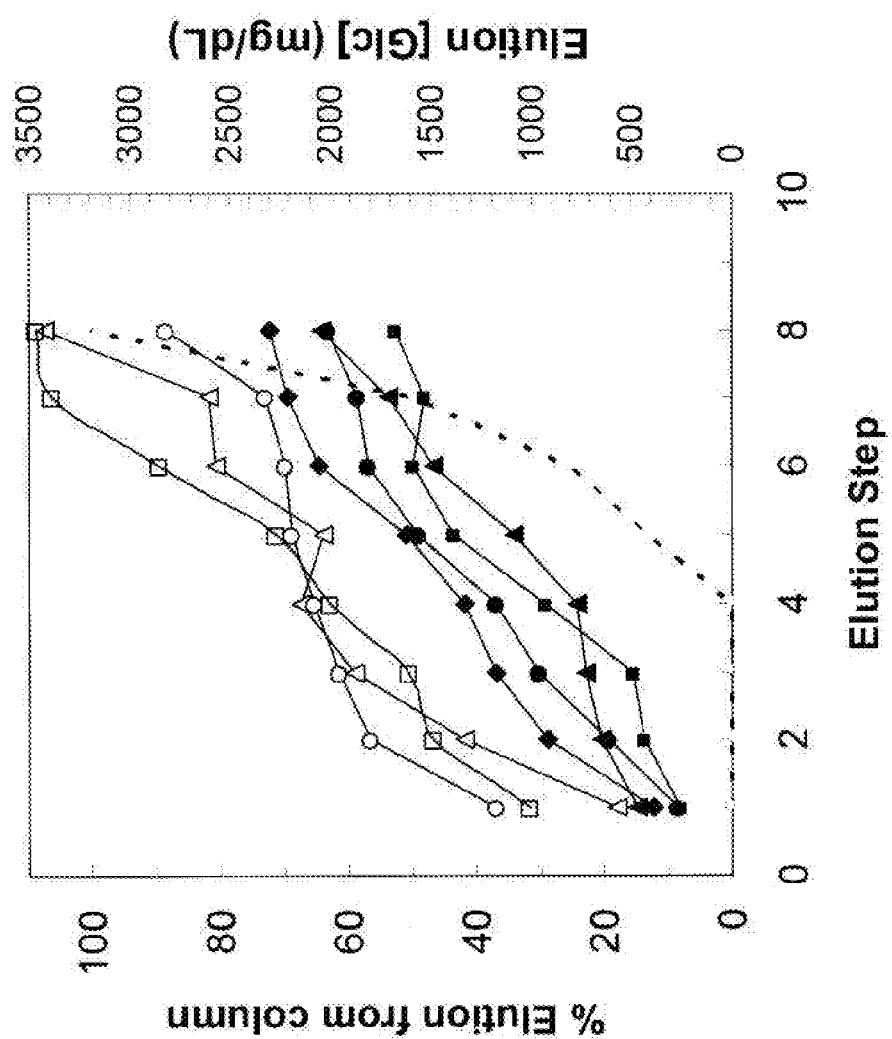
FIG. 4: shows individual monoclonal elution profiles from a glycogen bead column as a function of glucose. Open shapes—Monoclonals 1, 4 and 6. Closed shapes—Monoclonals 2, 3, 5, and 7. The dotted line refers to the glucose concentration used to elute at each step.

In order to determine the differences in monoclonal binding affinities for the glycogen resin, glycogen beads were added to a small column and washed extensively. The monoclonals were allowed to bind, and were then eluted with the binding step, followed by three wash steps with binding buffer. Next, the columns were eluted with 400, 800, 1600, and 3200 mg/dL glucose, and the optical density at 260 nm was measured at each step and plotted as a function of the original aptamer stock concentration (see FIG. 4). All monoclonals had an affinity for the glycogen beads, and all of them eluted from the column over a broad range of glucose values. However, a large portion (>50% of the total) of three of the bound sequences, 1, 4, and 6, washed off the beads even at zero glucose. Furthermore, >90% eluted from the column by 800 mg/dL, whereas <60% of the total amount bound for monoclonals 2, 3, 5, and 7 washed off the glycogen resin even at 3,200 mg/dl glucose. A comparison of the calculated secondary structure and sequence homology structure (FIG. 5) shows a strong correlation to the monoclonal glycogen-bead binding study results. Thus, the two sets of monoclonals provide two distinct pools of glycogen-binding aptamers with a range of low and high affinities, which could be used as a starting point for generating aptamers with a range of glycogen-binding affinities.

The structural homology between sequences was investigated using Mfold™ software, which is a free-energy minimization simulator to help predict possible secondary structures of the above monoclonals.

The structural results suggested that the evolved aptamer pool favors branched structures containing multiple 6 and 8 bp loops. Monoclonals 2, 3, and 7 contain nearly identical fold structures, and Monoclonal 5 contains some similarities to 2, 3, and 7. A re-examination of the monoclonal sequences (FIG. 5) shows that the 40 bp random region is very homologous between 2, 3, 5, and 7, and that the small differences in their sequences do not appear to affect their predicted fold structures. Monoclonals 4 and 6 differ dramatically in their sequence structure from the other 84 bp aptamers. Of particular note, however, is that the predicted fold structures for 4 and 6 share similar features to those of 2, 3, and 7.

Example 17

Monomeric Aptamer Pools with Varied Conjugate Binding Affinities

Mutating Monoclonals Separately to Create Diverse Pools of Binders cDNA monoclonals are made with manganese salts in PCR by mixing 6 uL of 10×PCR Buffer, 6 uL of dNTPs 2 mM, 24 uL each of 5' and 3' Primers, 6 uL of Taq Polymerase and the rest of the PCR tube volume is filled with $MnCl_2$ and distilled deionized $H_2O$ at a serial dilution of $MnCl_2$ between 2 mM to 0625 mM to find the right concentration of $MnCl_2$ as measured by agarose gel electrophoresis. PCR is then run @ 30 cycles @ 95° C. for 45 seconds, 53° C. for 45 seconds, and 72° C. for 1 minute.

SELEX Protocol

Mutated, modified RNA pools are mixed with protein-free Oyster glycogen (Type II, Sigma Aldrich) and allowed to equilibrate at 37 C. for 15 minutes. After this time, 100 ul of the glycogen/modified RNA solution is loaded onto a 1 mL capacity P-100 spin column equilibrated at 37 C., and the sample is centrifuged to remove unbound oligonucleotide, while allowing the glycogen-aptamer complex to pass through. A low concentration of glucose is added to the glycogen-aptamer mixture, which is passed through a fresh P-100 spin column again. This time, some aptamer-glycogen complex may be inhibited by glucose and stay in the spin column, while the glycogen is removed. The contents of the spin column, now free of glycogen, are simply eluted with 3×100 ul wash with binding buffer. The process is repeated for a range of glucose concentrations to obtain a diverse number of glucose pools. The obtained sequence(s) are reverse-transcribed into cDNA and amplified for the next round of transcription and selection. Monoclonal sequences can be obtained after several rounds of selection. The criteria for success includes measuring the A260 of the glycogen-aptamer complex as a function of glucose. If the pool is enriching toward higher glucose values then more aptamer should be bound to the glycogen, giving a measurably higher OD260 value for the glycogen-bound aptamer complex solution.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A conjugate comprising:
   an insulin molecule having an A-chain and a B-chain;
   an affinity ligand covalently bound to the A-chain; and
   a monovalent glucose binding agent covalently bound to the B-chain, wherein the monovalent glucose binding agent is a polynucleotide aptamer comprising the nucleotide sequence of SEQ ID NO: 1, 2, 3, 4, 5, 6, 7, 8, 9, or 10; and wherein the affinity ligand competes with glucose for non-covalent binding with the monovalent glucose binding agent.

2. The conjugate of claim 1, wherein in the absence of glucose, the monovalent glucose binding agent binds the affinity ligand to produce an inactive form of insulin.

3. The conjugate of claim 1, wherein in the presence of excess glucose, glucose competes with the affinity ligand for binding with the monovalent glucose binding agent to produce an active form of insulin.

4. The conjugate of claim 1, wherein the affinity ligand includes a saccharide selected from the group consisting of glucose, mannose, glucosamine, mannosamine, methylglucose, methylmannose, ethylglucose, and ethylmannose.

5. The conjugate of claim 1, wherein the monovalent glucose binding agent is chemically modified.

6. The conjugate of claim 1, wherein the monovalent glucose binding agent is pegylated.

7. A method comprising administering a conjugate of claim 1 to a patient in need thereof.

8. The method of claim 7, wherein the patient is diabetic.

9. A pharmaceutical composition comprising a conjugate of claim 1 and a pharmaceutically acceptable carrier.

10. A kit comprising a pharmaceutical composition of claim 9 and a syringe or pen.

11. The kit of claim 10, wherein the pharmaceutical composition is in a container separate from the syringe or pen.

12. The kit of claim 11, wherein the pharmaceutical composition comprises a non-liquid carrier and the kit further comprises a liquid carrier in a container separate from the syringe or pen.

* * * * *